US012564596B2

(12) United States Patent
Jennings et al.

(10) Patent No.: US 12,564,596 B2

(45) Date of Patent: Mar. 3, 2026

(54) AGENTS AND METHODS FOR MODULATING PATHOGEN ACTIVITY

(71) Applicants: Griffith University, Nathan (AU); Research Institute at Nationwide Children's Hospital, Columbus, OH (US)

(72) Inventors: Michael P. Jennings, Nathan (AU); Jennifer L. Edwards, Columbus, OH (US); Christopher J. Day, Nathan (AU); Johnson Mak, Nathan (AU)

(73) Assignees: Griffith University, Nathan (AU); Research Institute at Nationwide Children's Hospital, Columbus, OH (US)

(*) Notice: Subject to any disclaimer, the term of this patent is extended or adjusted under 35 U.S.C. 154(b) by 769 days.

(21) Appl. No.: 17/280,603

(22) PCT Filed: Sep. 30, 2019

(86) PCT No.: PCT/AU2019/051055

§ 371 (c)(1),
(2) Date: Mar. 26, 2021

(87) PCT Pub. No.: WO2020/061649

PCT Pub. Date: Apr. 2, 2020

(65) Prior Publication Data

US 2021/0338685 A1 Nov. 4, 2021

Related U.S. Application Data

(60) Provisional application No. 62/739,025, filed on Sep. 28, 2018.

(51) Int. Cl.

| | |
|---|---|
| ***A61K 31/55*** | (2006.01) |
| ***A61K 9/00*** | (2006.01) |
| ***A61K 31/196*** | (2006.01) |
| ***A61K 31/198*** | (2006.01) |
| ***A61P 31/04*** | (2006.01) |
| ***A61P 31/18*** | (2006.01) |

(52) U.S. Cl.

CPC ............ *A61K 31/55* (2013.01); *A61K 9/0014* (2013.01); *A61K 9/0039* (2013.01); *A61K 31/196* (2013.01); *A61K 31/198* (2013.01); *A61P 31/04* (2018.01); *A61P 31/18* (2018.01)

(58) Field of Classification Search

CPC ...... A61P 31/04; A61P 31/18; A61K 2300/00; A61K 31/196; A61K 31/198; A61K 31/55; A61K 45/06; A61K 9/0014; A61K 9/0019; A61K 9/0039; A61K 9/0053

See application file for complete search history.

(56) References Cited

U.S. PATENT DOCUMENTS

| | | | | |
|---|---|---|---|---|
| 4,835,138 A * | 5/1989 | Alexander | ........... | A61K 47/186 514/12.3 |
| 8,076,330 B2 | 12/2011 | Kroth | | |
| 9,238,016 B2 | 1/2016 | Kim et al. | | |
| 2004/0253222 A1 | 12/2004 | Apicella et al. | | |
| 2017/0087130 A1 | 3/2017 | Edwards et al. | | |
| 2019/0290607 A1* | 9/2019 | Orndorff | .............. | A61K 9/4808 |

FOREIGN PATENT DOCUMENTS

| | | | |
|---|---|---|---|
| CA | 2497582 | A1 | 3/2004 |
| CA | 2711221 | A1 | 7/2009 |
| CN | 108014111 | A | 5/2018 |
| CN | 108309983 | A | 7/2018 |
| EP | 1 207 886 | A2 | 5/2002 |
| RU | 2015129833 | | 1/2017 |
| WO | WO 2002/060936 | A2 | 8/2002 |
| WO | WO 2006/116157 | A2 | 11/2006 |
| WO | WO 2011/025696 | A1 | 3/2011 |
| WO | WO 2016/123063 | A1 | 8/2016 |

OTHER PUBLICATIONS

Extend European Search Report dated Jul. 7, 2022 in European Applicant No. 19864039.3.

Chavez-Dozal, A. A. et al., In vitro analysis of flufenamic acid activity against Candida albicans biofilms, International Journal of Antimicrobial Agents, vol. 43, pp. 86-91, 2014.

Dastidar, S. G. et al., Antibacterial property of methyl-DOPA & development of antibiotic cross-resistances in m-DOPA mutants, Indian Journal of Medical Research, vol. 86, pp. 142-147, 1986.

Dutta, N. K. et al., In Vitro and In Vivo Antimycobacterial Activity of an Antihypertensive Agent Methyl-L-DOPA, In Vivo, vol. 19, pp. 539-545, 2005.

Edwards, J. L. et al., The role of complement receptor 3 (CR3) in Neisseria gonorrhoeae infection of human cervical epithelia, Cellular Microbiology, vol. 3, No. 9, pp. 611-622, 2001.

Edwards, J. L. et al., A co-operative interaction between Neisseria gonorrhoeae and complement receptor 3 mediates infection of primary cervical epithelial cells, Cellular Microbiology, vol. 4, No. 9, pp. 571-584, 2002.

Hajishengallis, G. et al., Complement Receptor 3 Blockade Promotes IL-12-Mediated Clearance of Porphyromonas gingivalis and Negates Its Virulence In Vivo, Journal of immunology, vol. 179, pp. 2359-2367, 2007.

Inglot, A. D., Comparison of the Antiviral Activity in vitro of some Non-steroidal Anti-inflammatory Drugs. Journal of General Virology, vol. 4, pp. 203-214, 1969.

International Preliminary Report on Patentability in Australian Application No. PCT/AU2019/051055 dated Dec. 4, 2019 in 8 pages.

(Continued)

*Primary Examiner* — Jeffrey T. Palenik

(74) *Attorney, Agent, or Firm* — Knobbe, Martens, Olson & Bear, LLP

(57) ABSTRACT

Ligands of complement receptor 3, including ligands of the I domain of the alpha subunit of this receptor, are useful in methods, compositions and articles/devices for inhibiting the interaction of pathogens to a complement receptor 3-expressing cell and for treating or inhibiting the development of infections caused by such pathogens.

18 Claims, 23 Drawing Sheets

(56) References Cited

OTHER PUBLICATIONS

International Search Report in Australian Application No. PCT/AU2019/051055 dated Dec. 4, 2019 in 8 pages.
Jensen, M. R. et al., Structural Basis for Simvastatin Competitive Antagonism of Complement Receptor 3, The Journal of Biological Chemistry, vol. 291, No. 33, pp. 16963-16976, 2016.
Written Opinion in Australian Application No. PCT/AU2019/051055 dated Dec. 4, 2019 in 15 pages.
Cywes et al., Nonopsonic binding of *Mycobacterium tuberculosis* to human complement receptor type 3 expressed in Chinese hamster ovary cells, Infection and Immunology, 1996, vol. 64, No. 12, pp. 5373-5383.
Devine et al., Novel use of levodopa in human immunodeficiency virus encephalopathy-mediated parkinsonism in an adult, Journal of Postgrad Medicine, Jan. 2018, vol. 64, No. 1, pp. 53-55.
Jennings et al., Neisseria gonorrhoeae pilin glycan contributes to CR3 activation during challenge of primary cervical epithelial cells, Cellular Microbilogy, 2011, vol. 13, No. 6, pp. 885-896.
Kholodov et al., Clinical pharmacokinetics, Medicine, 1985, c. 83-98, 134-138, 160, 378-380.
Mintz et al., Levodopa therapy improves motor function in HIV-infected children with extrapyramidal syndromes, Neurology, 1996, vol. 47, No. 6, pp. 1583-1585.
Mishra et al., Expression of complement receptor 3 (CR3) and regulatory protein CD46 on dendritic cells of antiretroviral naïve and treated HIV-1 infected individuals: Correlation with immune activation status, Molecular Immunology. Apr. 2018, vol. 96, pp. 83-87.
Stoiber et al., Inhibition of HIV-1 infection in vitro by monoclonal antibodies to the complement receptor type 3 (CR3): an accessory role for CR3 during virus entry?, Molecular Immunology, 1997, vol. 34, No. 12-13, pp. 855-863.
Belikov, Pharmaceutical Chemistry, Higher school, M., 1993, T.1, c.43-47.
A short course in molecular pharmacology, ed. Sergeeva P.V., M., 1975, c.10.
Edwards et al., Targeting Complement Receptor 3 on Primary Human Cervical Cells has the Potential to Cure *Neisseria gonorrhoeae* Infection, Sex Transm Infect, vol. 95, Suppl 1, A1-A376, pp. A76-A77, 2019.
Kaiser, P., Anti-Integrin Therapy in Treatment Of DME, Retina Today, pp. 57-59, 2017.
Luminte, Compound Summary, PubChem CID 130476723, pp. 1-19, Retrieved on Oct. 13, 2022 from <https://pubchem.ncbi.nlm.nih.gov/compound/Luminate>; 2017.
European Search Report dated Feb. 1, 2024 for European Patent Application No. EP 23 20 9820, in 2 pages.

* cited by examiner

AGENTS AND METHODS FOR MODULATING PATHOGEN ACTIVITY

CROSS-REFERENCE TO RELATED APPLICATIONS

This application is the U.S. National Stage Application under 35 U.S.C. § 371 of International Application No. PCT/AU2019/051055, filed Sep. 30, 2019, designating the U.S. and published in English as WO 2020/061649 A1 on Apr. 2, 2020, which claims priority to U.S. Provisional Application No. 62/739,025 entitled "Agents and methods for modulating pathogen activity" filed 28 Sep. 2019, the contents of which are incorporated herein by reference in their entirety.

GOVERNMENT FUNDING

This invention was made with Government support under Grant No. NIH AI134848 awarded by the National Institutes of Health. The Government has certain rights in the invention.

FIELD OF THE INVENTION

This invention relates generally to the use of ligands of complement receptor 3, including ligands of the I domain of the alpha subunit of this receptor, in methods, compositions and articles/devices for inhibiting the interaction of pathogens to a complement receptor 3-expressing cell and for treating or inhibiting the development of infections caused by such pathogens.

BACKGROUND OF THE INVENTION

Integrins are cell surface receptors present in many organisms of kingdom Animalia, including the simple sponge and cnidarian (Burke R D, 1999. *Int Rev Cytol* 191:257-284; Hughes A L, 2001. *J Mol Evol* 52(1):63-72), and are frequently involved in cell adhesion to extracellular matrix proteins, cell-cell adhesion, and binding to complement-derived ligands (Giancotti F G & Ruoslahti E, 1999. *Science* 285(5430):1028-1032; Hynes R O, 2002. *Cell* 110(6):673-687). These receptors are composed of two transmembrane glycoprotein subunits, alpha (α) and beta (β), with different αβ combinations resulting in differing ligand specificity (Agramonte-Hevia J, et al., 2002. *FEMS Immuno/Med Microbiol* 34(4):255-266).

Complement receptor 3 (CR3, also known as Mac-1, CD11b/CD18, integrin $\alpha_m\beta_2$) is a member of the $\beta_2$ integrin family which also contains LFA-1 (CD11a/CD18, $\alpha_L/\beta_2$), p150/95 (CD11c/CD18, $\alpha_X/\beta_2$), and CD11d/CD18 ($\alpha_D\beta_2$) (Todd R F, 1996. *J Clin Invest* 98(1):1-2; Yakubenko V P, et al., 2008. *Exp Cell Res* 314(14):2569-2578). CR3 is expressed primarily on leukocytes, but is also known to be expressed on cervical (Edwards J L, et al., 2001, *Cell Microbiol.* 2001 3(9):611-22) and rectal epithelial cells (Hussain L A, et al., 1995. *Clin Exp Immunol* 102(2):384-388). Though the primary ligand of CR3 is iC3b, CR3 is a promiscuous receptor with a wide variety of reported ligands (Yakubenko V P, et al., 2002. *J Biol Chem* 277(50):48635-48642). Moreover, CR3 is used to promote infectious disease by several pathogens including Staphylococci (DuMont A L, et al., 2013. *Proc Natl Acad Sci USA* 110(26):10794-10799; Antal J M, et al., 1992. *Infect Immun* 60(3):1114-1121), streptococci (Orrskog S, et al., 2013. Mbio 4(1)), *Mycobacterium tuberculosis* (Cywes C, et al., 1996. *Infect Immun* 64(12):5373-5383), *Candida albicans* (Forsyth C B & Mathews H L, 1996. *Cell Immunol* 170(1):91-100), *Bordetella pertussis* (Reiman D, et al., 1990. *Cell* 61(7):1375-1382), and *Neisseria gonorrhoeae* (Edwards J L, et al., 2001, supra; Jennings M P, et al., 2011. *Cell Microbiol* 13(6):885-896).

The alpha subunit (CD11b) of CR3 contains an ~200-amino acid insertion domain, or I-domain, that is responsible for the binding of complement protein iC3b (Diamond M S, et al., 1993. *J Cell Biol* 120(4):1031-1043), as well as fibrinogen (Wright S D, et al., 1988. *Proc Natl Acad Sci USA* 85(20):7734-7738), intercellular adhesion molecule 1 (Diamond M S, et al., 1990 *J Cell Biol* 111(6 Pt 2):3129-3139), neutrophil inhibitory factor (Moyle M, et al., 1994. *J Biol Chem* 269(13):10008-10015), heparin (Diamond M S, et al., 1995. *J Cell Biol* 130(6):1473-1482), and a pilin disaccharide of *Neisseria gonorrhoeae* (Jennings M P, et al., 2011, supra). A crystal structure of the CD11b I-domain has shown the I-domain is a Rossmann fold protein with seven α-helices surrounding six β-sheets (McCleverty C J & Liddington R C, 2003. *Biochem J* 372(Pt 1):121-127). Previous studies have indicated that the CD11b I-domain has lectin function recognizing terminal galactose structures (Jennings M P, et al., 2011, supra).

SUMMARY OF THE INVENTION

The present invention is predicated in part on the unexpected finding that certain non-carbohydrate, small molecule ligands of the alpha subunit I-domain of CR3 are able to inhibit binding of pathogens with CR3-expressing cells and/or entry of pathogens into those cells. This finding has been reduced to practice in methods, compositions and articles for inhibiting interactions of pathogens with CR3-expressing cells and for inhibiting or treating pathogenic infections, as described hereafter.

Accordingly, in one aspect, the present invention provides methods for inhibiting an interaction of a pathogen with a CR3 polypeptide-expressing cell. These methods generally comprise, consist or consist essentially of contacting the cell with a non-carbohydrate, small molecule ligand of the alpha subunit I-domain of CR3, thereby inhibiting the interaction of the pathogen with the cell. The interaction may include one or both of binding of the pathogen to the cell and entry of pathogen into the cell. The cell may be an immune cell, illustrative examples of which include myeloid cells such as monocytes (e.g., macrophages including circulating macrophages and tissue-resident macrophages such as Kupffer cells), neutrophils, mast cells and dendritic cells, as well as lymphoid cells including leukocytes such as natural killer cells and cytotoxic T cells. Alternatively, the cell may be an epithelial cell, representative example of which include cervical epithelial cells, rectal epithelial cells and pharyngeal epithelial cells. The pathogen may be any pathogen that interacts with a CR3 polypeptide-expressing cell, including for example bacteria (e.g., *Neisseria, Streptococcus, Mycobacterium, Staphylococcus, Bordetella, Escherichia* and *Pseudomonas*), fungi (e.g., *Candida* and *Cryptococcus*), protozoa (e.g., *Toxoplasma*) and viruses (e.g., flaviviruses, orthomyxoviruses, paramyxoviruses, retroviruses, coronaviruses, filoviruses, arenaviruses, rhabdoviruses and herpesviruses).

Another aspect of the present invention provides methods of inhibiting or treating an infection of a subject with a pathogen that interacts with a complement receptor 3 (CR3) polypeptide-expressing cell. These methods generally comprise, consist or consist essentially of administering to the subject an effective amount of a non-carbohydrate, small molecule ligand of the alpha subunit I-domain of CR3, to thereby inhibit or treat the infection of the subject with the pathogen.

Still another aspect of the present invention provides methods of inhibiting or treating infection of a subject with a virus that interacts with a complement receptor 3 (CR3) polypeptide-expressing cell. These methods generally comprise, consist or consist essentially of administering to the subject an effective amount of a ligand of the alpha subunit I-domain of CR3, to thereby inhibit or treat infection of the subject with the virus. In specific embodiments, the virus is an enveloped virus, representative examples of which include flaviviruses, orthomyxoviruses, paramyxoviruses, retroviruses, coronaviruses, filoviruses, arenaviruses, rhabdoviruses and herpesviruses. In specific embodiments, the virus is a retrovirus such as human immunodeficiency virus (HIV). In specific embodiments, the effective amount is one that inhibits transmission of the virus to the subject and/or spreading of the virus within the subject.

In any of the aspects broadly described above and elsewhere herein, the ligand may be formulated for oral delivery, for systemic delivery or topical delivery. In some embodiments, the ligand is formulated for intrauterine delivery.

In any of the aspects broadly described above and elsewhere herein, the ligand may be concurrently administered with an antimicrobial agent.

In related aspects, the present invention provides topical compositions, suitably for inhibiting or treating an infection with a pathogen that interacts with a complement receptor 3 (CR3) polypeptide-expressing cell. These compositions generally comprise, consist or consist essentially of a non-carbohydrate, small molecule ligand of the alpha subunit I-domain of CR3, and optionally a pharmaceutically acceptable carrier. Suitably, the small molecule ligand is formulated for topical application to the skin or body cavity. In non-limiting examples of this type, the ligand is formulated as a foam, cream, wash, gel, spray, suppository, pessary, lotion, ointment, ovule, tampon, or aerosol. In some embodiments, the ligand is comprised in an article (e.g., coated on a surface of the article) such as a contraceptive device. In specific embodiments, the contraceptive device is an intrauterine device, intravaginal barrier, intravaginal sponge, male condom, or female condom.

In related aspects, the present invention provides compositions for intrauterine therapy or prophylaxis of an infection with a pathogen that interacts with a complement receptor 3 (CR3) polypeptide-expressing cell. These compositions generally comprise, consist or consist essentially of a non-carbohydrate, small molecule ligand of the alpha subunit I-domain of CR3, and optionally a pharmaceutically acceptable carrier.

A further aspect of the present invention provides articles, suitably for inhibiting or treating an infection with a pathogen that interacts with a complement receptor 3 (CR3) polypeptide-expressing cell. These articles generally comprise a non-carbohydrate, small molecule ligand of the alpha subunit I-domain of CR3 in an amount sufficient to inhibit or treat the infection in an individual wearing the article, and optionally a pharmaceutically acceptable carrier. In some embodiments, the article is selected from a glove, intrauterine device, vaginal dispenser, vaginal ring, intravaginal barrier-type device, intravaginal sponge, male condom, and female condom. In specific embodiments, the article is a contraceptive device, representative examples of which include intrauterine devices, intravaginal barriers, intravaginal sponges, male condoms and female condoms. The pathogen may be any pathogen that interacts with a CR3 polypeptide-expressing cell, including for example bacteria, yeast, parasites and viruses. In some embodiments, the pathogen is a virus, for example an enveloped virus, representative examples of which include orthomyxoviruses, paramyxoviruses, retroviruses, coronaviruses, filoviruses, arenaviruses, rhabdoviruses and herpesviruses. In specific embodiments, the virus is a retrovirus such as human immunodeficiency virus (HIV).

In any of the aspects broadly described above and elsewhere herein, the compositions may further comprise an antimicrobial agent.

The non-carbohydrate, small molecule ligand is typically an organic compound. In some embodiments, the ligand is a dibenzoazepine compound of Formula (I):

(I)

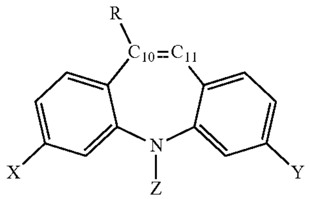

wherein:

R is hydrogen, hydroxyl, $NHC_{1-4}$alkyl, $OCOC_1$-alkyl or oxo;

X and Y are independently hydrogen or halogen;

Z is $C_{1-4}$ alkyl, $CONR^1R^2$, $C_{1-4}$alkylene$NR^1R^2$, $C_{1-4}$alkylene(NO)$R^1R^2$ or quinuclidinyl;

$R^1$ and $R^2$ are independently hydrogen or optionally substituted $C_{1-6}$alkyl; or $R^1$ and $R^2$ together with the nitrogen atom to which they are attached form a 3 to 8 membered heterocycloalkyl ring which may be optionally substituted; and the $C_{10}$-$C_{11}$ bond is a single or a double bond;

wherein when R is oxo, the $C_{10}$-$C_{11}$ bond is a single bond;

or a pharmaceutically acceptable salt or solvate thereof.

In some embodiments, the dibenzoazepine compound is selected from carbamazepine, oxcarbazepine, eslicarbazepine acetate, clomipramine, desipramine, imipramine, imipraminoxide, lofepramine, metapramine, opipramol, quinupramine and trimipramine. In specific embodiments, the dibenzoazepine compound is carbamazepine.

In any of the aspects broadly described above and elsewhere herein, the dibenzoazepine compound is administered, in some embodiments, at a dosage that is not effective for treating epilepsy.

In any of the aspects broadly described above and elsewhere herein, the dibenzoazepine compound is administered, in some embodiments, at a dosage that is not effective for treating neuropathic pain.

In any of the aspects broadly described above and elsewhere herein, the dibenzoazepine compound is administered, in some embodiments, at a dosage that is not effective for treating a bipolar disorder.

In other embodiments, the non-carbohydrate, small molecule ligand is an anthranilic acid derivative compound of Formula (II):

(II)

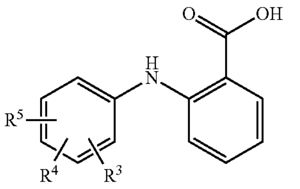

wherein:

$R^3$ is $C_{1-6}$alkyl, halogen or trifluoromethyl; and $R^4$ and $R^5$ are independently hydrogen, halogen, trifluoromethyl or $C_{1-6}$alkyl;

or a pharmaceutically acceptable salt or solvate thereof.

Suitably, the anthranilic acid derivative compound is selected from flufenamic acid, mefenamic acid, meclofenamic acid and tolfenamic add. In specific embodiments, the anthranilic acid derivative compound is flufenamic acid.

In any of the aspects broadly described above and elsewhere herein, in some embodiments, the pathogen whose infection is inhibited or treated with the anthranilic acid derivative compound is other than a Gram-positive bacterium.

In any of the aspects broadly described above and elsewhere herein, the anthranilic acid derivative compound is administered, in some embodiments, at a dosage that is not effective for providing analgesia.

In any of the aspects broadly described above and elsewhere herein, the anthranilic acid derivative compound is administered, in some embodiments, at a dosage that is not effective for treating inflammation.

In other embodiments, the non-carbohydrate, small molecule ligand is a phenylpropionic acid derivative compound of Formula (III):

(III)

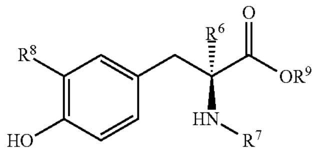

wherein:

$R^6$ is hydrogen, $CH_3$ or $CHF_2$;

$R^7$ is hydrogen or $NH_2$;

$R^8$ is hydrogen or OH;

$R^9$ is hydrogen or $C_{1-4}$alkyl;

or a pharmaceutically acceptable salt or solvate thereof.

The phenylpropionic acid derivative compound is suitably selected from methyldopa, carbidopa, methyldopa methyl ester, methyldopa ethyl ester, levodopa, etilevodopa (levodopa ethyl ester), metirosine, (α-methyltyrosine) and α-difluoromethyldopa. In specific embodiments, the phenylpropionic acid derivative compound is methyldopa.

In any of the aspects broadly described above and elsewhere herein, the phenylpropionic acid derivative compound is administered, in some embodiments, at a dosage that is not effective for treating hypertension.

In any of the aspects broadly described above and elsewhere herein, the phenylpropionic acid derivative compound is administered, in some embodiments, at a dosage that is not effective for treating stroke.

In any of the aspects broadly described above and elsewhere herein, the subject to whom the non-carbohydrate, small molecule ligand of the alpha subunit I-domain of CR3, in some embodiments, is administered is a female.

In any of the aspects broadly described above and elsewhere herein, the subject to whom the non-carbohydrate, small molecule ligand of the alpha subunit I-domain of CR3, in some embodiments, is administered is a male.

Figure 1:
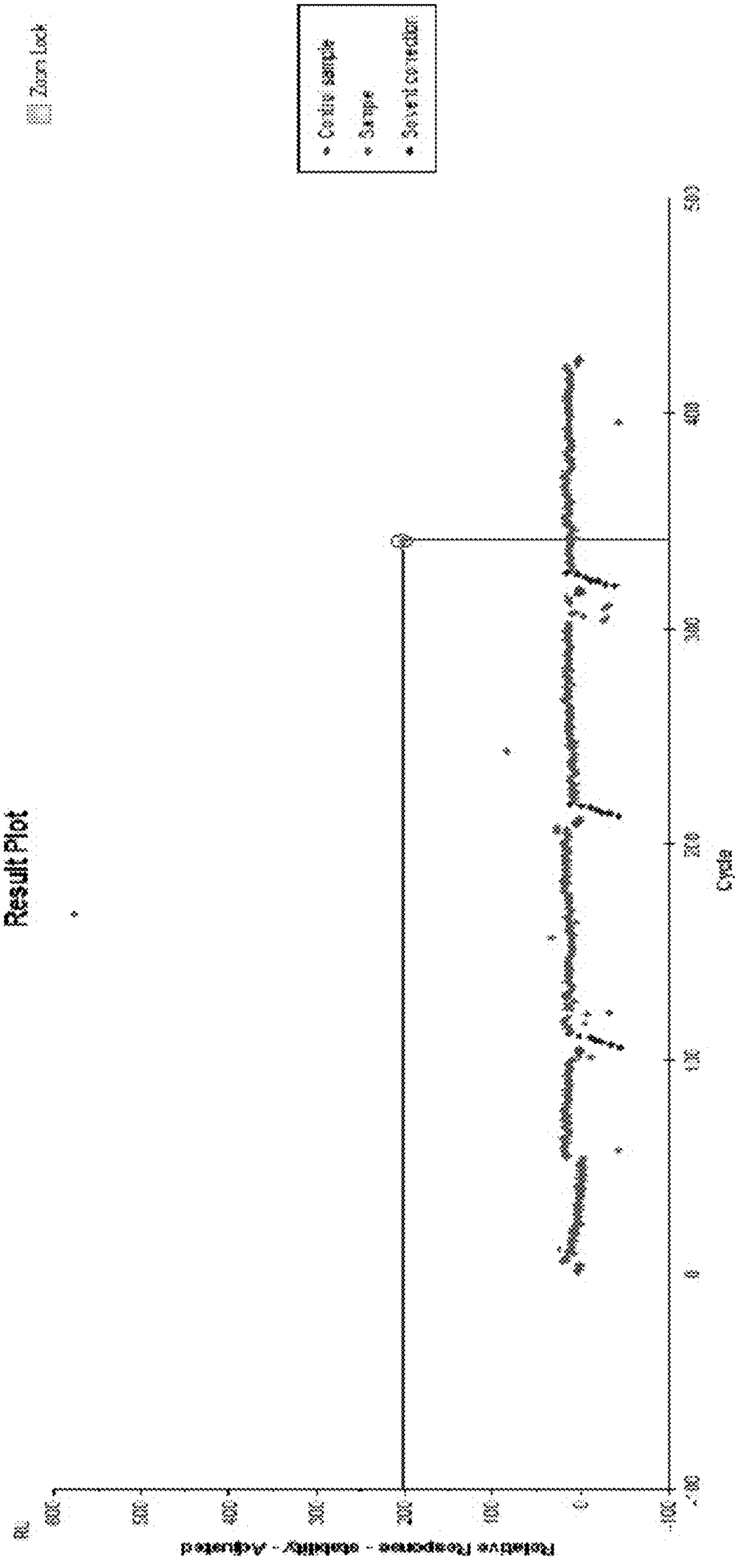
FIG. 1 is a graphical representation showing carbamazepine identification in a surface plasmon resonance screen. Highlighted spot is carbamazepine (CA sample #: SN00838842, molecular weight 236 g/mol). Green spots represent 384 drugs tested in screen. Red spots represent controls. Blue spots are solvent correction data points to allow for changes in refraction caused by the presence of 1% dimethyl sulfoxide (DMSO) in phosphate buffered saline (PBS).

Some figures and text contain color representations or entities. Color illustrations are available from the Applicant upon request or from an appropriate Patent Office. A fee may be imposed if obtained from a Patent Office.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

As used herein, unless otherwise specified, the term "alkyl" includes saturated aliphatic groups, including straight-chain alkyl groups (e.g., methyl, ethyl, propyl, butyl, pentyl, hexyl, etc.), and branched-chain alkyl groups (isopropyl, tert-butyl, iso-butyl, sec-butyl, etc.). The expression "$C_{x-y}$alkyl", wherein x is 1-2 and y is 2-6 indicates an alkyl group (straight- or branched-chain) containing the specified number of carbon atoms. For example, the term $C_{1-4}$alkyl includes methyl, ethyl, propyl, butyl, iso-propyl, tert-butyl, sec-butyl and iso-butyl. In some embodiments, a straight chain or branched chain alkyl has 4 or fewer carbon atoms (i.e., $C_{1-4}$). In some embodiments a straight chain or branched chain alkyl has 3 or fewer carbon atoms (i.e., $C_{1-3}$). Where indicated, an alkyl group may be substituted by one, two or three substituents. Non-limiting optional substituents for an alkyl group include halo; $CF_3$; $OR^a$; $SR^a$; $NR^aR^b$; and $COR^c$; wherein $R^a$ and $R^b$ are independently selected from hydrogen and $C_{1-4}$alkyl and RC is $C_{1-4}$alkyl or RC is phenyl optionally substituted with one, two or three substituents selected from halogen, $CF_3$, OH or $OC_{1-4}$alkyl.

As used herein, unless otherwise specified, the term "alkylene" includes saturated aliphatic linking groups, including straight-chain alkyl groups (e.g., methylene, ethylene, propylene, butylene etc.), and branched-chain alkyl groups (iso-propylene, tert-butylene, iso-butylene, sec-butylene). The expression "$C_{x-y}$alkylene", wherein x is 1-2 and y is 2-4 indicates an alkylene group (straight- or branched-chain) containing the specified number of carbon atoms. For example, the term $C_{1-4}$ alkylene includes methylene, ethylene, propylene, butylene, iso-propylene, tert-butylene, sec-butylene and iso-butylene. In some examples, a straight chain or branched chain alkylene has 4 or fewer carbon atoms (i.e., $C_{1-4}$). In some examples a straight chain or branched chain alkylene has 3 or fewer carbon atoms (i.e. $C_{1-3}$). In some preferred examples the alkylene linking group is propylene or sec-butylene.

The terms "administration concurrently" or "administering concurrently" or "co-administering" and the like refer to the administration of a single composition containing two or more agents, or the administration of each agent as separate compositions and/or delivered by separate routes either contemporaneously or simultaneously or sequentially within a short enough period of time that the effective result is equivalent to that obtained when all such agents are administered as a single composition. By "simultaneously" is meant that the agents are administered at substantially the same time, and desirably together in the same composition. By "contemporaneously" it is meant that the agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The agents may be administered in either order. The term "sequentially" as used herein means that the agents are administered in sequence, for example at an interval or intervals of minutes, hours, days or weeks. If appropriate the agents may be administered in a regular repeating cycle.

The term "antimicrobial agent" as used herein refers to any agent with antimicrobial activity, i.e., the ability to inhibit or reduce the growth and/or kill a microbe, e.g., by at least about 30%, at least about 40%, at least about 50%, at least about 75%, at least about 90% or more, as compared to in the absence of an antimicrobial agent. The term "antimicrobial agent" encompasses agents that that inhibit or reduce the growth and/or kill a microbe by directly interacting with the microbe and/or cells of the host in which the microbe resides or is located. Non-limiting examples of antimicrobial agents include a silver nanoparticle, a small molecule, a peptide, a peptidomimetics, an antibody or a fragment thereof, a nucleic acid, an enzyme (e.g., an antimicrobial metalloendopeptidase such as lysostaphin), an aptamer, a drug, an antibiotic, a chemical or any entity that can inhibit the growth and/or kill a microbe. Examples of an antimicrobial peptide that can be included in the compositions described herein, include, but are not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diarylquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof. Representative antimicrobial agents include, antibiotics, antifungals, antiprotozoals, antimalarials, antituberculotics and antivirals, and any mixtures thereof.

Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "CR3 polypeptide", "complement receptor 3" and "CR3" are interchangeably used herein to refer to a heterodimer polypeptide comprising a 165-kDa alpha chain (CD11b; integrin $\alpha_M$), non-covalently linked to a 95-kDa beta chain (CD18; integrin $\beta_2$). CR3 which is also known as also known as Mac-1, integrin $\alpha_M\beta_2$, or CD11b/CD18, is a member of the $\beta_2$ (CD18) integrin family. CR3 is a pattern recognition receptor, capable of recognizing and binding to many molecules found on the surfaces of invading pathogens. The major ligand-binding site in CR3 is the $\alpha_M$ subunit-inserted domain (I-domain), so named because it is inserted, in sequence, between the N and C-termini of the larger, seven-bladed β-propeller domain.

As used herein, the term "CR3 polypeptide-expressing cell" refers to a cell that expresses a CR3 polypeptide. Representative cells that express a CR3 polypeptide include myeloid cells such as monocytes (e.g., macrophages including circulating macrophages and tissue-resident macrophages such as Kupffer cells), neutrophils, mast cells and dendritic cells, as well as lymphoid cells including leukocytes such as natural killer cells and cytotoxic T cells, as well as epithelial cells such as cervical epithelial cells, rectal epithelial cells and pharyngeal epithelial cells.

By "effective amount", in the context of treating or preventing a condition is meant the administration of an amount of an agent or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials. Non-limiting symptoms of pathogen infections include acute febrile illness, malaise, fatigue, headache, flushing, diarrhea, nausea, vomiting, coughing, abdominal pain, myalgias and, in severe disease, production of pro-inflammatory mediators, including pro-inflammatory cytokines and vascular leakage.

As used herein, the term "epithelial cell" encompasses all cells lining an organ including, but not limited to, endothelial cells, mesothelial cells, and urothelial cells, that may be squamous, columnar, or cuboidal Simple squamous cells can be found lining blood vessels, lymph vessels, the mesothelium of body cavities, and the ascending thin limb of the kidney. Stratified squamous cells are found lining the hard palate, the dorsum of the tongue, the gingival, the esophagus, rectum, anus, skin, cervix, vagina, labia majora, oropharynx, cornea, and the external urethra orifice. Simple columnar cells can be found in the ducts on the submandibular glands, attached gingiva, ductuli, epididymis, vas deferens, seminal vesicle, larynx, trachea, nose, membranous urethra, penile urethra, the stomach, small and large intestine, rectum, gallbladder, ductal and lobular epithelium, fallopian tubes, uterus, endometrium, cervix, ejaculatory duct, bulbourethral glands, and prostate. Stratified columnar epithelial cells can be found in the ducts of the submandibular glands attached gingival, ductuli epididymis, vas deferens, seminal vesicle, larynx, trachea, nose, membranous urethra, and penile urethra. Simple cuboidal cells can be found in thyroid follicles, ependyma, the ovaries, tubuli recti, rete testis, respiratory bronchioles, and the proximal and distal convoluted tubules of the kidney. Stratified cuboidal cells can be found in the sweat gland ducts.

The term "expression" refers the biosynthesis of a gene product. For example, in the case of a coding sequence, expression involves transcription of the coding sequence into mRNA and translation of mRNA into one or more polypeptides. Conversely, expression of a non-coding sequence involves transcription of the non-coding sequence into a transcript only.

As used herein, the term "halogen" includes fluorine, bromine, chlorine and iodine. Similarly, the term "halo" includes fluoro, chloro, bromo and iodo. In some examples, halo is preferably chloro.

As used herein, unless otherwise stated, the term "heterocycloalkyl" refers to saturated cyclic aliphatic groups containing 3- to 8-members including at least one endocyclic N atom, and optionally further including one or two further heteroatoms wherein a heteroatom replaces an endocyclic carbon atom. Preferred heteroatoms are nitrogen, oxygen and sulfur. In some embodiments a heteroatom is nitrogen or oxygen. The heterocycloalkyl moiety may be monocyclic or it may be a fused or bridged ring system. Preferably the heterocycloalkyl moiety is monocyclic. Examples of heterocycloalkyl rings formed when $R^1$ and $R^2$ together with the nitrogen atom to which they are attached form a 3 to 8 membered ring, include pyrrolidinyl and piperidinyl. Further examples include aziridinyl, azetidinyl and azepinyl. In some embodiments, the heterocycloalkyl ring has 4 to 6 members, preferably 5 or 6 members. In addition to the N atom, the heterocyclic ring may include one or more additional endocyclic heteroatoms selected from O, S and N to replace a carbon atom, for example morpholinyl and piperazinyl. A piperazinyl ring may be substituted on an endocyclic C or N atom. Optional substituents for a heterocycloalkyl group include $C_{1-4}$alkyl optionally substituted by $OR^d$, $SR^d$, $CF_3$, $NR^dR^e$ or halogen; wherein $R^d$ and $R^e$ are independently selected from hydrogen and $C_{1-4}$alkyl.

As used herein, the terms "modulating", "regulating" and their grammatical equivalents refer to an effect of altering a biological activity or effect (e.g., binding of a ligand to the alpha subunit I-domain of a CR3 polypeptide). For example, a ligand of a particular receptor may modulate the activity of that receptor by either increasing/stimulating, or decreasing/inhibiting the activity or effect of the receptor. In the context of ligand binding to the alpha subunit I-domain of a CR3 polypeptide, the ligand may modulate the activity of the CR3 polypeptide by inhibiting entry of a pathogen into a cell that expresses the CR3 polypeptide.

As used herein, unless otherwise defined, the term "optionally substituted" refers to substitution of a hydrogen atom on a group, for example an alkyl, phenyl or heterocycloalkyl group, with a non-hydrogen moiety as detailed herein. Any substituted group may bear one, two, three, or more optional substituents. In some examples, a substituted group will have one substituent.

It is also to be understood that definitions given to the variables of the generic formulae described herein will result in molecular structures that are in agreement with standard organic chemistry definitions and atom valencies.

As used herein, the term "immune cell" refers to a cell belonging to the immune system. Immune cells include cells of hematopoietic origin such as but not limited to T lymphocytes (T cells), B lymphocytes (B cells), natural killer (NK) cells, granulocytes, neutrophils, macrophages, monocytes, dendritic cells, and specialized forms of any of the foregoing, e.g., Kupffer cells, plasmacytoid dendritic cells, Langerhans cells, plasma cells, natural killer T (NKT) cells, T helper cells, and cytotoxic T lymphocytes (CTL).

The term "ligand", as used herein, refers to any molecule which is capable of binding a receptor.

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such as from the genus Macaca (e.g., cynomolgus monkeys such as Macaca fascicularis, and/or rhesus monkeys (Macaca mulatta)) and baboon (Papio ursinus), as well as marmosets (species from the genus Callithrix), squirrel monkeys (species from the genus Saimiri) and tamarins (species from the genus Saguinus), as well as species of apes such as chimpanzees (Pan troglodytes), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (e.g., snakes, frogs, lizards etc.), and fish. In specific embodiments, the subject is a primate such as a human. However, it will be understood that the terms "patient," "subject," "host" or "individual" do not imply that symptoms are present.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

The term "pharmaceutically acceptable salt" as used herein is a broad term, and is to be given its ordinary and customary meaning to a person of ordinary skill in the art (and is not to be limited to a special or customized meaning), and refers without limitation to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17.sup.th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the term "solvate" is a complex of variable stoichiometry formed by a solute [in this invention, a compound of Formulae (I), (II) or (III)] and a solvent. Such solvents should preferably not interfere with the biological activity of the solute. Solvents may be, by way of example, water, acetone, ethanol or acetic acid. Methods of solvation are generally known in the art. It will be appreciated that the solvate is preferably pharmaceutically acceptable. In some embodiments, a solvate is a hydrate, for example a mono-, di- or tri-hydrate. Compounds of Formulae (I), (II) and (III) may be in the form of a solvate, for example, a hydrate such as a monohydrate or dihydrate, or a sesquihydrate.

The term "receptor" refers to a cell-associated protein that binds to a bioactive molecule termed a "ligand". This interaction mediates the effect of the ligand on the cell. Receptors can be membrane bound, cytosolic or nuclear; monomeric (e.g., thyroid stimulating hormone receptor, beta-adrenergic receptor) or multimeric (e.g., complement receptor 3, PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

As used herein a "small molecule" refers to a compound that has a molecular weight of less than 3 kilodaltons (kDa), and typically less than 1.5 kilodaltons, and suitably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, less than 1.5 kilodaltons, less than about 1 kDa or even less than about 0.5 kDa.

As used herein, the terms "treatment", "treating", and the like, refer to obtaining a desired pharmacologic and/or physiologic effect. The effect may be therapeutic in terms of a partial or complete cure for a disease or condition (e.g., a hematologic malignancy) and/or adverse effect attributable to the disease or condition. These terms also cover any treatment of a condition or disease in a mammal, particularly in a human, and include: (a) inhibiting the disease or condition, i.e., arresting its development; or (b) relieving the disease or condition, i.e., causing regression of the disease or condition.

Each embodiment described herein is to be applied mutatis mutandis to each and every embodiment unless specifically stated otherwise.

2. Compounds, Compositions and Articles for Modulating Pathogens Interactions with CR3 Polypeptide Expressing Cells The present invention is based in part on the identification of non-carbohydrate, small molecule ligands of the alpha subunit I-domain of CR3, which are able to inhibit binding of pathogens with CR3 polypeptide-expressing cells and/or entry of pathogens into those cells. In some embodiments, these ligands are also able to treat CR3 polypeptide-expressing cells that have already been infected with a pathogen. Notably, because these ligands do not act on the pathogen but rather block pathogen-CR3 I-domain interactions, they may serve in some embodiments as novel agents for inhibiting or treating infections with pathogens that are resistant to antimicrobials such as antibiotics. The ligands have utility in inhibiting or treating pathogenic infections of a range of CR3 polypeptide-expressing cells including immune cells and epithelial cells. The cell may be an immune cell, illustrative examples of which include myeloid cells such as monocytes (e.g., macrophages including circulating macrophages and tissue-resident macrophages such as Kupffer cells), neutrophils, mast cells and dendritic cells, as well as lymphoid cells including leukocytes such as natural killer cells and cytotoxic T cells. Alternatively, the cell may be an epithelial cell, representative example of which include cervical epithelial cells, rectal epithelial cells and pharyngeal epithelial cells. Based on these finding, the present invention provides methods, compositions and articles for inhibiting interactions of pathogens with CR3-expressing cells and for inhibiting or treating pathogenic infections.

2.1 CR3 Polypeptide Ligands

The methods, compositions and articles of the present invention feature non-carbohydrate, small molecule ligands of the alpha subunit I-domain of CR3. In some embodiments, the ligand is a dibenzoazepine compound of Formula (I):

(I)

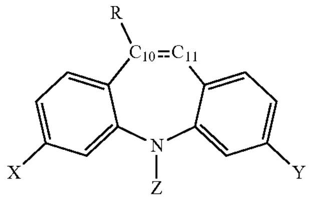

wherein:

R is hydrogen, hydroxyl, $NHC_{1-4}$alkyl, $OCOC_{1-4}$alkyl or oxo;

X and Y are independently hydrogen or halogen;

Z is $C_{1-4}$ alkyl, $CONR^1R^2$, $C_{1-4}$alkylene$NR^1R^2$, $C_{1-4}$alkylene(NO)$R^1R^2$ or quinuclidinyl;

$R^1$ and $R^2$ are independently hydrogen or optionally substituted $C_{1-6}$alkyl;

or $R^1$ and $R^2$ together with the nitrogen atom to which they are attached form a 3 to 8 membered heterocycloalkyl ring which may be optionally substituted; and the $C_{10}$-$C_{11}$ bond is a single or a double bond;

wherein when R is oxo, the $C_{10}$-$C_{11}$ bond is a single bond, or a pharmaceutically acceptable salt or solvate thereof.

In some embodiments, R is hydrogen, hydroxyl, $NHCH_3$, $OCOCH_3$ or oxo. In some examples R is hydrogen.

In some embodiments, X and Y are independently hydrogen or Cl.

Representative examples of Z substituents include $CH_3$, $CONR^1R^2$, $C_{3-4}$alkylene$NR^1R^2$, or 3-quinuclidinyl. A particular Z substituent is $CONH_2$.

In some embodiments, $R^1$ and $R^2$ are both hydrogen. When $R^1$ and $R^2$ are $C_{1-6}$alkyl, in some embodiments they are independently $C_{1-4}$alkyl.

In some particular embodiments, the moiety $NR^1R^2$ in the compounds of Formula (I) or (Ia) is methylamino, ethylamino, n-propylamino, isopropylamino, n-butylamino, methyl-ethylamino, diethylamino, di-n-propylamino, di-n-butylamino, methyl-n-butylamino, pyrrolidinyl, piperidinyl, piperazinyl or morpholinyl.

Certain representative examples of Z include $C_{1-4}$alkyl, for example $CH_3$; $CONH_2$; $C_{3-4}$alkylene$NR^1R^2$, wherein $R^1$ and $R^2$ are independently optionally substituted $CH_3$ or hydrogen; 3-quinuclidinyl. Particular examples of Z include $CH_3$, $CONH_2$, $(CH_2)_3NHCH_3$; $(CH_2)_3N(CH_3)_2$; $(CH_2)_3(NO)(CH_3)_2$; $CH_2CH_2(CH_3)CH_2N(CH_3)_2$; $(CH_2)_3N(CH_3)CH_2CO$(4-chlorophenyl); $(CH_2)_3$(piperazineethanol) and 3-quinuclidinyl.

A particular compound of Formula (I) is carbamazepine [5H-dibenzo[b,f]azepine-5-carboxamide; CAS 298-46-4]:

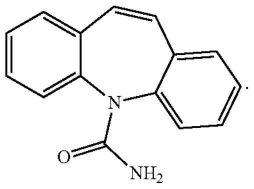 [SMILES: NC(=O)N1c2ccccc2C=Cc2ccccc21]

Further examples of dibenzoazepine compounds of Formula (I) include:

a) Oxcarbazepine [11,10-dihydro-10-oxo-5H-dibenzo(b,f)azepine-5-carboxamide];

b) Eslicarbazepine acetate [(S)-10-acetoxy-10,11-dihydro-5H-dibenzo[b,f]azepine-5-carboxamide];

c) Clomipramine [3-(3-chloro-10,11-dihydro-5H-dibenzo[b,f]azepin-5-yl)-N,N-dimethylpropan-1-amine];

d) Desipramine [3-(10,11-dihydro-5H-dibenzo[b,f]azepin-5-yl)-N-methylpropan-1-amine];

e) Imipramine [3-(10,11-dihydro-5H-dibenzo[b,f]azepin-5-yl)-N,N-dimethylpropan-1-amine];

f) Imipraminoxide [3-(5,6-dihydrobenzo[b][f]benzazepin-11-yl)-N,N-dimethylpropan-1-amine N-oxide];

g) Lofepramine [N-(4-chlorobenzoylmethyl)-3-(10,11-dihydro-5H-dibenzo[b,f]azepin-5-yl)-N-methyl-propan-1-amine];

h) Metapramine (±)-10,11-dihydro-N,5-dimethyl-5H-dibenz[b,f]azepin-10-amine];

i) Opipramol [4-[3-(5H-dibenz[b,f]azepin-5-yl)propyl]-1-piperazinethanol];

j) Quinupramine [(±)-11-quinuclidin-3-yl-5,6-dihydrobenzo[b][1]benzazepine also known as 11-(1-azabicyclo[2.2.2]octan-3-yl)-5,6-dihydrobenzo[b][1]benzazepine]; and k) Trimipramine [(±)-3-(10,11-dihydro-5H-dibenzo[b,f]azepin-5-yl)-N,N-2-trimethylpropan-1-amine].

In particular embodiments, the compound of Formula (I) is a compound represented by a compound of Formula (Ia):

(Ia)

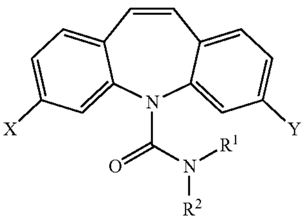

wherein:

X and Y are independently hydrogen or halogen;

$R^1$ and $R^2$ are independently hydrogen or $C_{1-6}$alkyl;

or $R^1$ and $R^2$ together with the nitrogen atom to which they are attached form a 3 to 8 membered heterocycloalkyl ring;

or a pharmaceutically acceptable derivative thereof.

In a preferred embodiment, the compound of Formula (Ia) is carbamazepine.

In other embodiments, the non-carbohydrate, small molecule ligand is an anthranilic acid derivative compound of Formula (II):

(II)

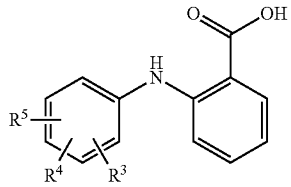

wherein:

$R^3$ is $C_{1-6}$alkyl, halogen or trifluoromethyl; and $R^4$ and $R^5$ are independently hydrogen, halogen, trifluoromethyl or $C_{1-6}$alkyl;

or a pharmaceutically acceptable salt or solvate thereof.

Compounds of Formula (II) are also known as fenamates.

In some embodiments, when any of the $R^3$, $R^4$ or $R^5$ substituents is halogen, preferably it is Cl.

Suitably, when any of $R^3$, $R^4$ or $R^5$ substituents is $C_{1-6}$alkyl, it is $C_{1-4}$alkyl, such as $CH_3$, $C_2H_5$ or $C_3H_2$, preferably $CH_3$.

In some embodiments, one of $R^4$ and $R^5$ is hydrogen.

In some embodiments, $R^4$ and $R^5$ are both hydrogen. In non-limiting examples, $R^3$ is trifluoromethyl.

A particular example of a compound of Formula (II) is Flufenamic acid [2{[3-(trifluoromethyl)phenyl]amino}benzoic acid]:

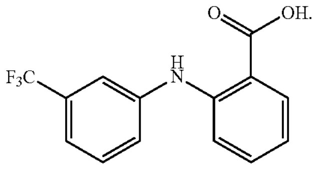 [SMILES: O=C(O)c1ccccc1Nc1cccc(C(F)(F)F)c1]

Other examples of compounds of Formula (II) include:

a) Mefenamic acid
[2-(2,3-dimethylphenyl)aminobenzoic acid];

b) Meclofenamic acid
[2-[(2,6-dichloro-3-methylphenyl)amino]benzoic acid]; and c) Tolfenamic acid
[2-[(3-chloro-2-methylphenyl)amino]benzoic acid].

In other embodiments, the non-carbohydrate, small molecule ligand is phenylpropionic derivative compound of Formula (III):

(II)

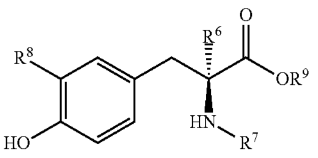

wherein:

$R^6$ is hydrogen, $CH_3$ or $CHF_2$;

$R^7$ is hydrogen or $NH_2$;

$R^9$ is hydrogen or OH;

$R^9$ is hydrogen or $C_{1-4}$alkyl;

or a pharmaceutically acceptable salt or solvate thereof.

In some embodiments, $R^6$ is $CH_3$.

In some embodiments, $R^9$ is OH.

Suitably, when $R^9$ is $C_{1-4}$alkyl, it is $C_2H_5$ or $CH_3$.

In some embodiments, $R^9$ is hydrogen.

Suitably, $R^6$ and $R^9$ are not both hydrogen.

A preferred compound of Formula (III) is methyldopa [(S)-2-amino-3-(3,4-dihydroxyphenyl)-2-methyl-propanoic acid]:

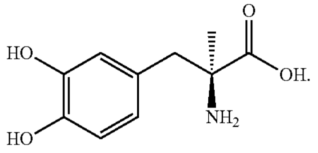

Further examples of compounds of Formula (III) include:

a) Carbidopa
[(S)-3-(3,4-dihydroxyphenyl)-2-hydrazino-2-methylpropanoic acid];

b) Methyldopa methyl ester
[methyl (2S)-2-amino-3-(3,4-dihydroxyphenyl)-2-methyl-propanoate];

c) Methyldopa ethyl ester
[ethyl (2S)-2-amino-3-(3,4-dihydroxyphenyl)-2-methyl-propanoate];

d) Levodopa
[(S)-2-amino-3-(3,4-dihydroxyphenyl)propanoic acid];

e) Etilevodopa (Levodopa ethyl ester)
[(S)-2-amino-3-(3,4-dihydroxyphenyl)propanoic acid];

f) Metirosine, (α-methyltyrosine)
[(2S)-2-amino-3-(4-hydroxyphenyl)propanoic acid]; and g) α-Difluoromethyldopa
[(2S)-2-amino-2-(3,4-dihydroxyphenyl)methyl-3,3-difluoro-propanoic acid]

It will be appreciated that the structures of some of the compounds of this invention may include asymmetric centres, including asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques or by stereochemically controlled synthesis. Furthermore, the structures and other compounds and moieties discussed in this application also include all tautomers thereof.

Compounds of Formulae (I), (II) and (III) as described herein may be purchased from commercial sources such a chemical manufacturers or suppliers well known to the skilled person. Alternatively, the compounds may be synthesised from commercially available starting materials and/or synthetic intermediates using art recognized synthetic routes. Many of the compounds described are known drug molecules, also referred to as active pharmaceutical ingredients (APIs), and have received regulatory approval for alternative indications to those described herein. Synthetic routes to drug molecules, such as those encompassed by compounds of Formulae (I), (II) and (III), are referenced herein in or are described in, for example, Ruben Vandanyan and Victor Hruby (2006) Synthesis of Essential Drugs (Elsevier Science) or Ruben Vandanyan and Victor Hruby (2016) Synthesis of Best-Seller Drugs (Academic Press), and references therein.

Compounds of Formula (I) are readily available from commercial sources, or may be prepared by synthetic routes well known in the art. For example, compounds of Formula (Ia) are disclosed in U.S. Pat. No. 2,948,718 (Geigy Chemical Corporation) which is herein incorporated by reference in its entirety. Other compounds of Formula (I) may be sourced from commercial suppliers. Alternatively, a compound of Formula (I) may be prepared by published synthetic routes such as those described below, or by routes analogous to those described in the literature.

For example, a compound of Formula (I) may be synthesised by reacting the corresponding intermediate (IV):

(IV)

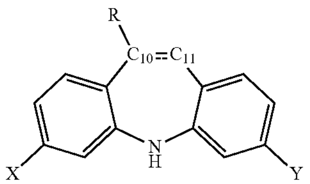

wherein X, Y and R are as defined above for compounds of Formula (I);

with a compound CI-Z; wherein Z is a substituent as described herein for compounds of Formula (I).

Conditions for such a reaction are well known in the art, and include use of a reagent such as sodium hydride.

A compound of Formula (I) wherein Z is $CONR^1R^2$ may be prepared by reacting a compound of Formula (V) with phosgene to provide the corresponding carbonyl chloride intermediate which is then reacted with the required amine ($HNR^1R^2$) to form a compound of Formula (I). Alternatively, compounds of Formula (I) wherein $R^1$ and $R^2$ are alkyl or $R^1$ and $R^2$ together with the nitrogen atom to which they are attached form a heterocycloalkyl group may be synthesised by reacting the intermediate (IV) with the appropriate carbamic acid chloride ($ClCONR^1R^2$). When $R^1$ is an alkyl substituent and $R^2$ is hydrogen, the intermediate (IV) may be reacted with the appropriate alkyl isocyanate ($O{=}C{=}NR^1$).

Intermediates of Formula (IV) are available from commercial sources or may be readily prepared by published methods for the preparation of dibenzoazepine compounds.

Carbamazepine [5H-dibenzo[b,f]azepine-5-carboxamide, also known as 2-azatricyclo-[9.4.0.$0^{3,8}$]pentadeca-1(15),3,5,7,9,11,13-heptaene-2-carboxamide] may be purchased from, for example, Merck KGaA or Sigma-Aldrich, Inc [CAS No. 298-46-4]. Carbamazepine may be synthesised according to the route described in U.S. Pat. No. 2,948,718 (Geigy Chemical Corporation) or U.S. Pat. No. 6,245,908 (Jubilant Organosys Ltd).

The following compounds are also commercially available from a number of chemical manufacturers and suppliers, such as Merck KGaA or Sigma-Aldrich, Inc and the like.

Oxcarbazepine [11,10-dihydro-10-oxo-SH-dibenzo(b,f) azepine-5-carboxamide] is commercially available [CAS No. 28721-07-5]. It may be synthesised according to the route described in GB Patent No. 1310571 (Ciba-Geigy AG) or US Patent Application No. 20030004154.

Eslicarbazepine acetate [(S)-10-acetoxy-10,11-dihydro-5H-dibenzo[b,f]azepine-5-carboxamide] is commercially available [CAS No. 236395-14-5]. It may be synthesised according to the route described in U.S. Pat. No. 5,753,646 (Bial Portela CA and SA).

Clomipramine [3-(3-chloro-10,11-dihydro-5H-dibenzo[b,f]azepin-5-yl)-N,N-dimethylpropan-1-amine] [CAS No. 303-49-1] is commercially available as its hydrochloride salt [CAS No. 17321-77-6]. Clomipramine may be synthesised according to the route described in U.S. Pat. No. 3,515,785 (Geigy Chemical Corp).

Desipramine [3-(10,11-dihydro-5H-dibenzo[b,f]azepin-5-yl)-N-methylpropan-1-amine] [CAS No. 50-47-5] is commercially available in the form of a hydrochloride salt [CAS No. 58-28-6]. Desipramine may be prepared according to the synthetic method of U.S. Pat. No. 3,454,554 (Colgate Palmolive Co).

Imipramine [3-(10,11-dihydro-5H-dibenzo[b,f]azepin-5-yl)-N,N-dimethylpropan-1-amine] [CAS No. 50-49-7] is commercially available as the hydrochloride salt [CAS No. 113-52-0], as a pamoate salt [CAS NO. 10075-24-8] or as the N-oxide derivative, Imipraminoxide [CAS No. 6829-98-7]. Imipramine may be synthesised using the route described in U.S. Pat. No. 2,554,736 (JR Geigy A G).

Lofepramine [N-(4-chlorobenzoylmethyl)-3-(10,11-dihydro-5H-dibenzo[b,f]azepin-5-yl)-N-methyl-propan-1-amine][CAS No. 23047-25-8] is commercially available from, for example, Key Organics, Camelford, UK as a hydrochloride salt [CAS No. 26786-32-3]. It may be prepared using the route described in WO 2008/139484.

Metapramine [(±)-10,11-dihydro-N,5-dimethyl-5H-dibenz[b,f]azepin-10-amine] is commercially available from various sources. [CAS No. 21730-16-5]. It may be prepared according to the procedure described in U.S. Pat. No. 3,622,565 (Rhone-Poulenc S A).

Opipramol [4[3-(5H-dibenz[b,f]azepin-5-yl)propyl]-1-piperazinethanol] [CAS No. 315-72-0] is commercially available as the free base [CAS No. 315-72-0] and as the dihydrochloride salt [CAS No. 909-39-7]. Opipramol may be prepared according to the method of DE 1142870B (JR Geigy AG).

Quinupramine [(±)-11-quinuclidin-3-yl-5,6-dihydrobenzo[b][1]benzazepine also known as 11-(1-azabicyclo [2.2.2]octan-3-yl)-5,6-dihydrobenzo[b][1]benzazepine] [CAS No. 31721-17-2] is commercially available as a hydrochloride salt or as a tartrate salt.

Trimipramine [(±)-3-(10,11-dihydro-5H-dibenzo[b,f]azepin-5-yl)-N,N-2-trimethylpropan-1-amine] [CAS No. 739-71-9] is available commercially as its maleate salt [CAS No. 521-78-8].

Further examples of compounds of Formula (I) may be prepared according to analogous routes to those described above.

Compounds of Formula (II) are available from commercial sources or may be readily prepared by known synthetic routes for the preparation of anthranilic acid derivatives, for example through the well-known reaction of potassium 4-bromobenzoate with the appropriate aniline substituted with the required $R^3$, $R^4$ and $R^5$ substituents.

Flufenamic acid [2{[3-(trifluoromethyl)phenyl] amino}benzoic acid] [CAS No. 530-78-9] is readily available from commercial sources and may be obtained from, for example, Merck KGaA or Sigma-Aldrich, Inc. Flufenamic acid may be synthesised using published synthetic routes such as the method described in U.S. Pat. No. 4,980,498 (Merckle GmbH).

Mefenamic acid [2-(2,3-dimethylphenyl)aminobenzoic acid] [CAS No. 61-68-7] may be obtained from commercial suppliers such as Merck KGaA or Sigma-Aldrich, Inc. It may also be synthesised using methodology such as that described in U.S. Pat. No. 3,138,636 (Parke Davis and Co, LLC) or CN 105949075.

Meclofenamic acid [2-[(2,6-dichloro-3-methylphenyl) amino]benzoic acid] is available as the sodium salt, meclofenate sodium, from, for example Merck KGaA or Sigma-Aldrich, Inc [CAS No. 67254-91-5]. Synthesis of meclofenamic acid is described in, for example, U.S. Pat. No. 3,313,848 (Parke Davis and Co, LLC).

Tolfenarnic add [2-[(3-chloro-2-methylphenyl)amino] benzoic acid] is available from Merck KGaA or Sigma-Aldrich, Inc (CAS No. 13710-19-5). The synthesis of tolfenamic acid is described in U.S. Pat. No. 4,092,430 (Ciba-Geigy Corp).

Further examples of compounds of Formula (II) may be prepared from the corresponding 4-bromobenzoate and substituted aniline according to analogous routes to those described above.

Compounds of Formula (III) are readily available from commercial sources or may be prepared by published synthetic routes.

Methyldopa is readily available from commercial sources such as Cayman Chemical, Merck KGaA or Sigma-Aldrich, Inc in the form of methyldopa sesquihydrate][CAS No. 41372-08-1], methyldopa methyl ester hydrochloride [CAS No. 5123-53-5] and methyldopa ethyl ester [CAS No. 6014-30-8]. Methyldopa may be synthesised according to the route described in U.S. Pat. No. 2,868,818 (Merck & Co Inc)

Carbidopa is available from commercial sources, for example Merck KGaA or Sigma-Aldrich, Inc, in the form of carbidopa monohydrate [CAS No. 38821-49-7]. Carbidopa may be synthesised according to the route described in U.S. Pat. No. 3,462,536 (Merck & Co Inc).

α-Difluoromethyldopa may be prepared according to the method of G. Zbinden et al., Inhibition of 5-hydroxytryptophan nephrotoxicity by α-Difluoromethyldopa, an inhibitor of L-amino acid decarboxylase, Toxicology Letters, Vol 5, Issue 2, February 1980, pp 125-129.

Levodopa is readily available from a variety of commercial suppliers such as Sigma-Aldrich, Inc. [CAS No. 59-92-7] and Etilevodopa (Levodopa ethyl ester) is available from, for example Merck KGaA or Sigma-Aldrich, Inc [CAS No. 37178-37-3]. Levodopa may be synthesised according to published methods, such as the route described in U.S. Pat. No. 4,962,223 (MURST).

Metirosine, (α-methyltyrosine) is commercially available from, for example, Sigma-Aldrich, Inc. [CAS No. 672-87-7]. It may be synthesised using the route described in, for example, U.S. Pat. No. 2,868,818 (Merck & Co, Inc).

Pharmaceutically acceptable salts are described in, for example, *Handbook of Pharmaceutical Salts*: Properties, Selection, and Use; Edited by P. Heinrich Stahl and Camile G. Wermuth. VHCA, Verlag Helvetica Chimica Acta, Zürich, Switzerland, and Wiley-VCH, Weinheim, Germany. 2002. Their methods of preparation are well known in the art.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, pamoic acid and the like. For example, an amine group of the compounds of the invention may undergo reaction with an acid, for example hydrochloric acid, to form an acid addition salt, for example a hydrochloride or a dihydrochloride. Examples of salts of compounds of Formula (I) include methanesulphonate, hydrochloride, hydrobromide, acetate, (L)-tartate, phosphate, and sulphate. Examples of salts of compounds of Formula (II) include hydrochloride, dihydrochloride, maleate and pamoate. Examples of salts of compounds of Formula (III) include hydrochloride.

Pharmaceutically acceptable base addition salts may be prepared from inorganic and organic bases. Corresponding counterions derived from inorganic bases include the sodium, potassium, lithium, ammonium, calcium and magnesium salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, choline, betaine, ethylenediamine, glucosamine, N-alkylglucamines, theobromine, purines, piperazine, piperidine, and N-ethylpiperidine. For example, where the compound of the invention possesses a carboxylic acid group or a phenol group, the compound may undergo reaction with a base to form the base addition salt. A particular salt is a sodium salt.

2.2 Pharmaceutical Compositions

While it is possible that, for use in therapy, a compound described herein may be administered in an undiluted form, however it is preferable to present a compound of Formula (I), (II) or (III) as a pharmaceutical composition.

A pharmaceutical composition may comprise a compound of Formula (I), (II) or (III) and a pharmaceutically acceptable carrier. Carriers must be "acceptable" in the sense of being compatible with the other ingredients of the composition and not deleterious to the recipient thereof.

In accordance with the invention, a compound as described is administered under a therapeutic regime that is non-toxic to the subject.

The pharmaceutical compositions of the present invention or the compositions used in the methods of the present invention may be formulated and administered using methods known in the art. Techniques for formulation and administration may be found in, for example, *Remington: The Science and Practice of Pharmacy*, Loyd V. Allen, Jr (Ed), The Pharmaceutical Press, London, 22nd Edition, September 2012.

The compositions of the invention may be formulated for administration by any route. In some embodiments the composition is formulated for oral administration. An oral composition may be in the form of tablets, capsules, powders, granules, or liquid preparations. In some embodiments the composition is formulated for topical administration. A topical composition may be in the form of a cream, lotion, ointment, or gel. In some embodiments the composition is formulated for parenteral administration, for example by an intramuscular, intrathecal, intraperitoneal, intravaginal, intrauterine, intravesical or intravenous route.

Suitable unit dosages and maximum daily dosages of a compound of Formula (I), (II) or (III) may be determined in accordance with the unit doses and maximum daily doses used conventionally. Accordingly, may be administered to a patient at a daily dosage of, for example, from 250 mg to 750 mg every 6 hours to 500 mg to 1 g every 6 to 8 hours, with a maximum dose of approximately 50 mg/Kg/day or 4 g/day.

A compound of Formula (I), (II) or (III) as herein described, may be the sole active ingredient administered to the subject. However, it will be appreciated that the compound may be administered with another therapeutic agent (e.g., an antimicrobial agent). For example, the compound may be administered with one or more further therapeutic agents in combination. The combination may allow for concurrent administration (e.g., separate, sequential or simultaneous administration) of the compound with the other active ingredient(s). The combination may be provided in the form of a pharmaceutical composition. Administration with one or more other active ingredients is within the scope of the invention. In specific embodiments, a compound of Formula (I), (II) or (III) as herein described may be administered concurrently with an antimicrobial agent, which includes without limitation compounds that kill or inhibit the growth of microorganisms such as viruses, bacteria, yeast, fungi, protozoa, etc. and thus include antibiotics, antifungals, antiprotozoals, antimalarials, antituberculotics and antivirals. Illustrative antibiotics include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol. Representative antivirals include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, valganciclovir, zalcitabine, zanamivir, and zidovudine. Non-limiting examples antiprotozoals include atovaquone, chloroquine hydrochloride, chloroquine phosphate, metronidazole, metronidazole hydrochloride, and pentamidine isethionate. Anthelmintics can be at least one selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, bifonazole, butoconazole, chlordantoin, chlorphenesin, ciclopirox olamine, clotrimazole, eberconazole, econazole, fluconazole, flucytosine, flutrimazole, griseofulvin microsize, griseofulvin ultramicrosize, itraconazole, isoconazole, itraconazole, ketoconazole, miconazole, nifuroxime, nystatin, terbinafine hydrochloride, tioconazole, terconazole and undecenoic acid. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Antituberculotics include but are not restricted to clofazimine, cycloserine, dapsone, ethambutol hydrochloride, isoniazid, pyrazinamide, rifabutin, rifampin, rifapentine, and streptomycin sulfate.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the compound care should be taken to ensure that the activity of the compound is not destroyed in the process and that the compound is able to reach its site of action without being destroyed. In some circumstances it may be necessary to protect the compound by means known in the art, such as, for example, micro encapsulation or coating (such as the use of enteric coating). Similarly the route of administration chosen should be such that the compound reaches its site of action.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, and reducing agents such as methionine or sulphite.

The compounds as herein described, or pharmaceutically acceptable salt thereof, may be prepared in parenteral dosage forms, including those suitable for intravenous, intrathecal, and intracerebral or epidural delivery. The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

The solvent or dispersion medium for the injectable solution or dispersion may contain any of the conventional solvent or carrier systems for the compound, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolarity, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection, intravesicular administration or infusion.

Sterile injectable solutions are prepared by incorporating the active compound in the required amount in the appropriate solvent with various of the other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of a compound of Formula (I), (II) or (III), in which the active compound may be formulated with an inert diluent or with an edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, and a sweetening agent, preservative, dye or flavouring.

Any component used in the preparation of any dosage unit form should be pharmaceutically pure and substantially non-toxic in the amounts employed.

The present invention also extends to any other forms suitable for administration, for example topical application such as creams, foams, washes, lotions, sprays, and gels; enteral formulations such as suppositories; or compositions suitable for inhalation or intranasal delivery, for example solutions, aerosols, dry powders, suspensions or emulsions. In specific embodiments, the compounds of the present invention are formulated for topical application to the skin or body cavity, such as foams, creams, washes, gels, sprays, suppositories, pessaries, lotions, ointment, ovule, tampon, or aerosol. The topical applications may be provided via an article to be worn by or placed in a subject. For example, the article may be a glove, intrauterine device, vaginal dispenser, vaginal ring, or a contraceptive device such as an intravaginal barrier-type device, intravaginal sponge, male condom or female condom.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It may be advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 μg to about 200 mg. Expressed in proportions, the active compound may be present in from about 0.25 μg to about 200 mg/mL of carrier. In the case of compositions containing supplementary active ingredients, the dosages are determined by reference to the usual dose and manner of administration of the said ingredients.

3. Methods for Modulating Pathogen Interactions with CR3 Polypeptide Expressing Cells The compounds and compositions of the present invention have utility in inhibiting an interaction (e.g., binding and/or entry) of a pathogen with a CR3 polypeptide-expressing cell, and in inhibiting or treating an infection of a subject (e.g., a male subject or a female subject) with a pathogen that interacts with CR3 polypeptide-expressing cell. Numerous CR3 polypeptide-expressing cells are known in the art, including for example immune cells and epithelial cells. Representative examples of immune cells include myeloid cells such as monocytes (e.g., macrophages including circulating macrophages and tissue-resident macrophages such as Kupffer cells), neutrophils, mast cells and dendritic cells, as well as lymphoid cells which include leukocytes such as natural killer cells and cytotoxic T cells. Non-limiting examples of epithelial cells include cervical epithelial cells, rectal epithelial cells and pharyngeal epithelial cells.

A range of pathogens interact with CR3 polypeptide-expressing cells, including bacteria, fungi, protozoa and viruses.

Non-limiting examples of bacteria, including pathogenic bacteria, belong to the genera *Bacillus, Bordetella, Borrelia, Brucella, Campylobacter, Chlamydia, Chlamydophila, Clostridium, Corynebacterium, Enterobacter, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella,*

*Shigella, Staphylococcus, Streptococcus, Treponema, Vibrio*, and *Yersinia*. Non-limiting examples of specific pathogenic bacterial species include a strain of *Bacillus anthracis*, a strain of a strain of *Bordetella pertussis*, a strain of a strain of *Borrelia burgdorferi*, a strain of a strain of *Brucella abortus*, a strain of a strain of *Brucella canis*, a strain of a strain of *Brucella melitensis*, a strain of a strain of *Brucella suis*, a strain of a strain of *Campylobacter jejuni*, a strain of *Chlamydia pneumonia*, a strain of *Chlamydia trachomatis*, a strain of *Chlamydophila psittaci*, a strain of *Clostridium botulinum*, a strain of *Clostridium difficile*, a strain of *Clostridium perfringens*, a strain of *Clostridium tetani*, a strain of *Corynebacterium diphtheria*, a strain of *Enterobacter sakazakii*, a strain of *Enterococcus faecalis*, a strain of *Enterococcus faecium*, a strain of *Escherichia coli*, a strain of *Francisella tularensis*, a strain of *Haemophilus influenza*, a strain of *Helicobacter pylori*, a strain of *Legionella pneumophila*, a strain of *Leptospira interrogans*, a strain of *Listeria monocytogenes*, a strain of *Mycobacterium leprae*, a strain of *Mycobacterium tuberculosis*, a strain of *Mycobacterium ulcerans*, a strain of *Mycoplasma pneumonia*, a strain of *Neisseria gonorrhoeae*, a strain of *Neisseria meningitides*, a strain of *Pseudomonas aeruginosa*, a strain of *Rickettsia rickettsia*, a strain of *Salmonella typhi* and *Salmonella typhimurium*, a strain of *Shigella sonnei*, a strain of *Staphylococcus aureus*, a strain of *Staphylococcus epidermidis*, a strain of *Staphylococcus saprophyticus*, a strain of *Streptococcus agalactiae*, a strain of *Streptococcus pneumonia*, a strain of *Streptococcus pyogenes*, a strain of *Treponema pallidum*, a strain of *Vibrio cholera*, a strain of *Yersinia enterocolitica*, and a strain of *Yersinia pestis*.

Representative examples of fungi, including pathogenic fungi, belong to the genera *Aspergillus, Candida, Cryptococcus, Histoplasma, Pneumocystis*, and *Stachybotrys*. Non-limiting examples of specific pathogenic fungi species include a strain of *Aspergillus clavatus, Aspergillus fumigatus, Aspergillus flavus, Candida albicans, Cryptococcus albidus, Cryptococcus gattii, Cryptococcus laurentii, Cryptococcus neoformans, Histoplasma capsulatum, Pneumocystis jirovecii, Pneumocystis carinii*, and *Stachybotrys chartarum*.

Non-limiting examples of protozoa, including pathogenic protozoa, belong to the genera *Acanthamoeba, Balamuthia, Cryptosporidium, Dientamoeba, Endolimax, Entamoeba, Giardia, lodamoeba, Leishmania, Naegleria, Plasmodium, Sappinia, Toxoplasma, Trichomonas*, and *Trypanosoma*. Non-limiting examples of specific pathogenic protozoa species include a strain of *Acanthamoeba* spp., *Balamuthia mandrillaris, Cryptosporidium canis, Cryptosporidium fells, Cryptosporidium hominis, Cryptosporidium meleagridis, Cryptosporidium muris, Cryptosporidium parvum, Dientamoeba fragilis, Endolimax nana, Entamoeba dispar, Entamoeba hartmanni, Entamoeba histolytica, Entamoeba coli, Entamoeba moshkovskii, Giardia lamblia, lodamoeba butschlii, Leishmania aethiopica, Leishmania braziliensis, Leishmania chagasi, Leishmania donovani, Leishmania infantum, Leishmania major, Leishmania mexicana, Leishmania tropica, Naegleria fowleri, Plasmodium falciparum, Plasmodium knowlesi, Plasmodium malariae, Plasmodium ovale, Plasmodium vivax, Sappinia diploidea, Toxoplasma gondii, Trichomonas vaginalis, Trypanosoma brucei*, and *Trypanosoma cruzi*.

Representative examples of viruses, including pathogenic viruses, may be selected from Picornaviruses (e.g., polio virus, foot and mouth disease virus), Caliciviruses (e.g., SARS virus, feline infectious peritonitis virus), Togaviruses sindbis virus, the equine encephalitis viruses, chikungunya virus, rubella virus, Ross River virus, bovine diarrhea virus, hog cholera virus), Flaviviruses (e.g., dengue virus, West Nile virus, yellow fever virus, Japanese encephalitis virus, St. Louis encephalitis virus, tick-borne encephalitis virus), Coronaviruses (e.g., human coronaviruses (common cold), swine gastroenteritis virus), Rhabdoviruses (e.g., rabies virus, vesicular stomatitis viruses), Filoviruses (e.g., Marburg virus, Ebola virus.), Paramyxoviruses (e.g., measles virus, canine distemper virus, mumps virus, parainfluenza viruses, respiratory syncytial virus, Newcastle disease virus, rinderpest virus), Orthomyxoviruses (e.g., human influenza viruses, avian influenza viruses, equine influenza viruses), Bunyaviruses (e.g., hantavirus, LaCrosse virus, Rift Valley fever virus), Arenaviruses (e.g., Lassa virus, Machupo virus), Reoviruses (e.g., human reoviruses, human rotavirus), Birnaviruses (e.g., infectious bursal virus, fish pancreatic necrosis virus), Retroviruses (e.g., HIV 1, HIV 2, HTLV-1, HTLV-2, bovine leukemia virus, feline immunodeficiency virus, feline sarcoma virus, mouse mammary tumor virus), Hepadnaviruses (e.g., hepatitis B virus.), Parvoviruses (e.g., human parvovirus B, canine parvovirus, feline panleukopenia virus) Papovaviruses (e.g., human papillomaviruses, SV40, bovine papillomaviruses), Adenoviruses (e.g., human adenovirus, canine adenovirus, bovine adenovirus, porcine adenovirus), Herpes viruses (e.g., herpes simplex viruses, varicella-zoster virus, infectious bovine rhinotracheitis virus, human cytomegalovirus, human herpesvirus 6), and Poxviruses (e.g., vaccinia, fowlpoxviruses, raccoon poxvirus, skunkpox virus, monkeypoxvirus, cowpox virus, musculum contagiosum virus).

Because the compounds and compositions of the present invention are able to inhibit pathogen interaction with a CR3 polypeptide-expressing cell, they are useful in methods of inhibiting or treating an infection of a subject with a pathogen that interacts with a CR3 polypeptide-expressing cell, in which an effective amount of a non-carbohydrate, small molecule ligand of the invention is administered to the subject, to thereby inhibit or treat the infection of the subject with the pathogen.

Modes of administration, amounts of ligand administered, and ligand-containing compositions, for use in the methods of the present invention, are routine and within the skill of practitioners in the art. Whether an infection, particularly a pathogenic infection, has been treated or inhibited is determined by measuring one or more diagnostic parameters indicative of the course of the disease, compared to a suitable control. In the case of an animal experiment, a "suitable control" is an animal not treated with a ligand inhibitor of the invention, or treated with the pharmaceutical composition without the ligand inhibitor. In the case of a human subject, a "suitable control" may be the individual before treatment, or may be a human (e.g., an age-matched or similar control) treated with a placebo. In accordance with the present invention, the treatment or inhibition of development of an infection includes and encompasses without limitation: (1) impairing, abrogating, reducing, preventing, or arresting the development of, the infection in a subject; (2) treating an infection in a subject; or (3) preventing the development of an infection in a subject that has a predisposition to the infection but has not yet been diagnosed with the infection and, accordingly, the treatment constitutes prophylactic treatment of the infection.

The compositions and methods of the present invention are thus suitable for treating an individual who has been diagnosed with an infection, who is suspected of having an infection, who is known to be susceptible and who is considered likely to develop an infection, or who is considered likely to develop a recurrence of a previously treated infection.

In order that the invention may be readily understood and put into practical effect, particular preferred embodiments will now be described by way of the following non-limiting examples.

EXAMPLES

Example 1

Figure 2:
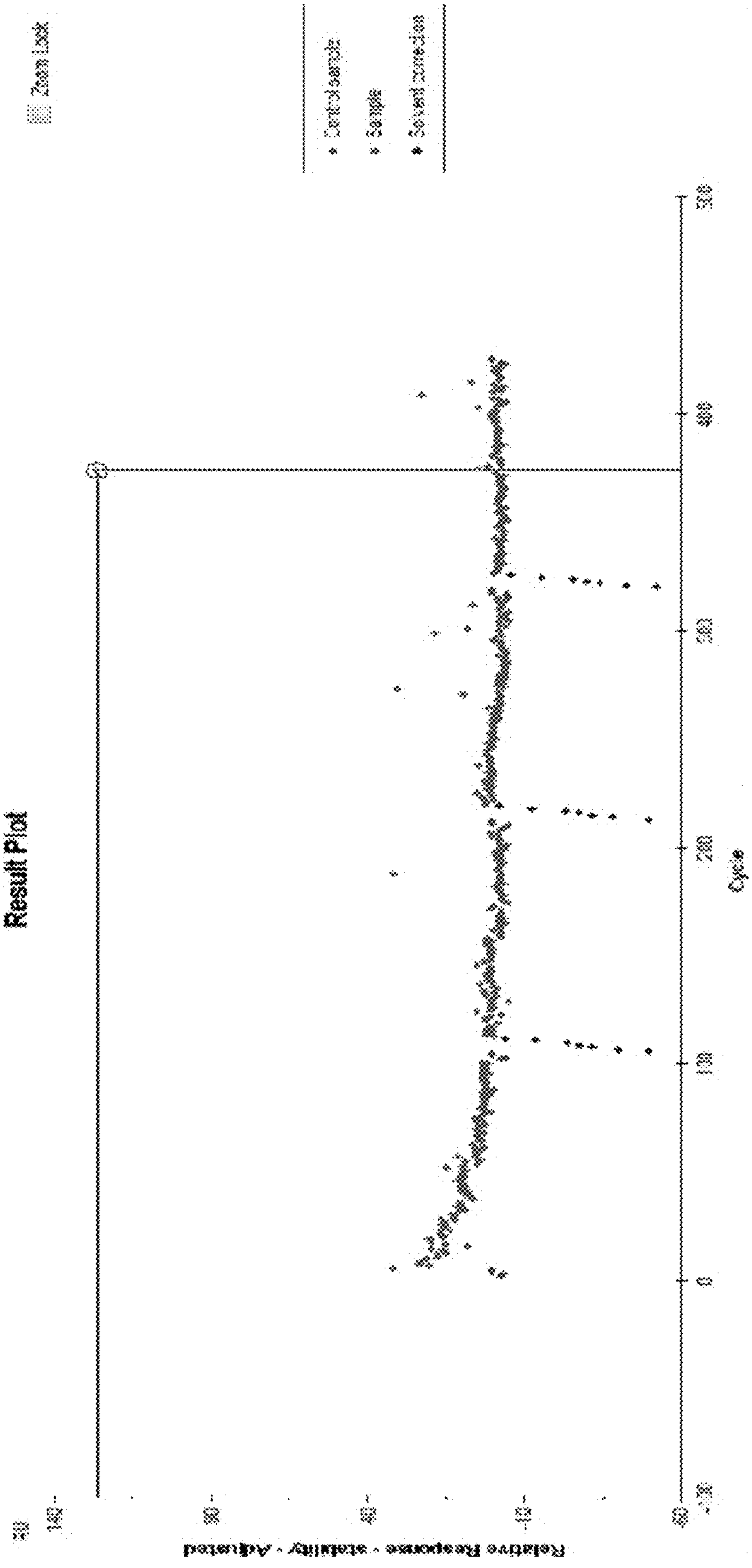
FIG. 2 is a graphical representation showing flufenamic acid identification in a surface plasmon resonance screen. Highlighted spot is flufenamic acid (CA sample #: SN01004628, molecular weight 281 g/mol). Green spots represent 384 drugs tested in screen. Red spots represent controls. Blue spots are solvent correction data points to allow for changes in refraction caused by the presence of 1% DMSO in PBS.
Figure 3:
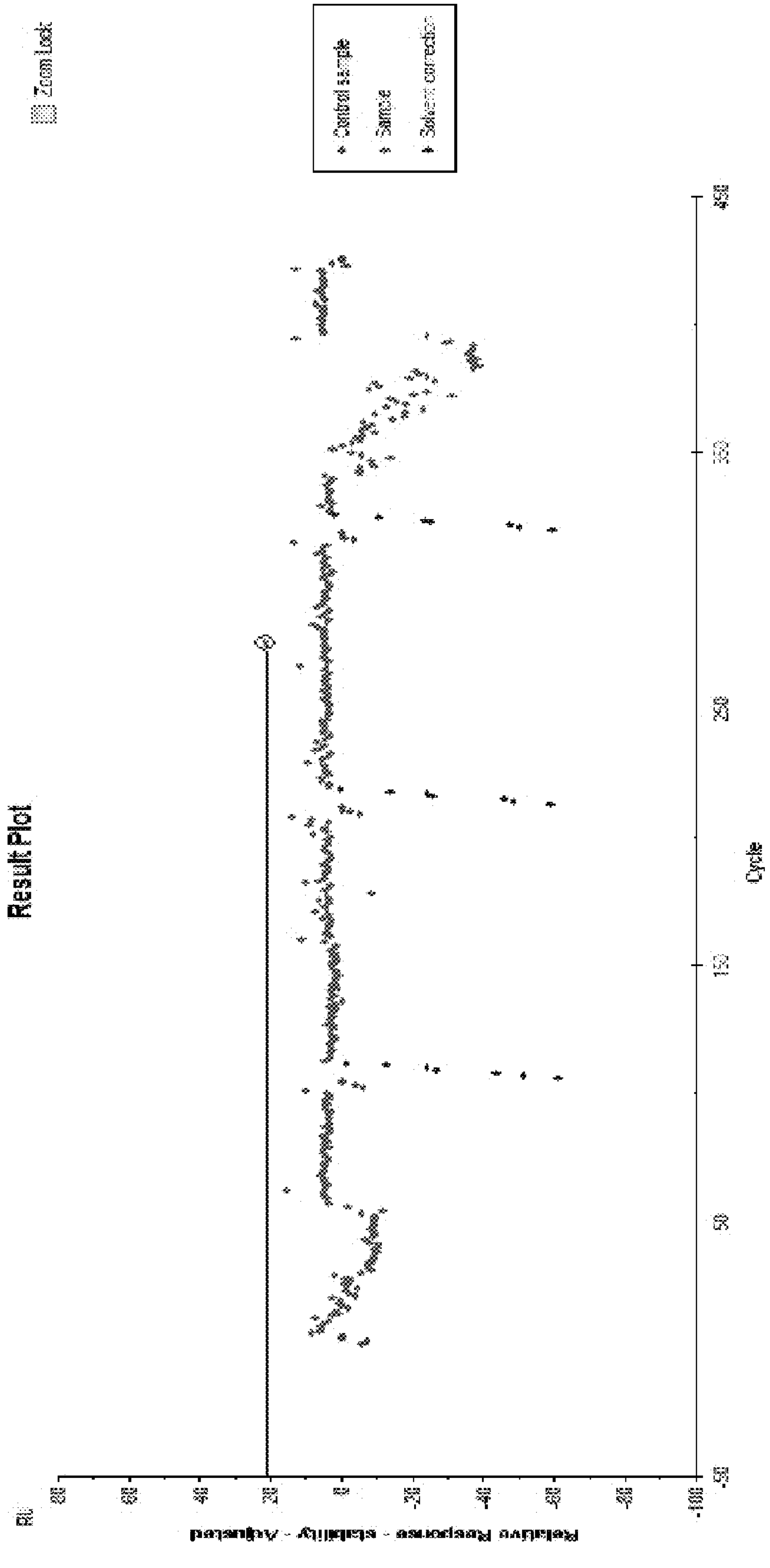
FIG. 3 is a graphical representation showing methyldopa identification in a surface plasmon resonance screen. Highlighted spot is methyldopa (CA sample #: SN01004410, molecular weight 211 g/mol). Green spots represent 384 drugs tested in screen. Red spots represent controls. Blue spots are solvent correction data points to allow for changes in refraction caused by the presence of 1% DMSO in PBS.

Screening Drug Libraries to Identify Drugs that Bind CR3 and Screening for a Subset of Drugs that Block CR3 *Neisseria gonorrhoeae* Pilin Interaction and CR3 HIV Interaction A recombinant I-domain (rI-domain) of human CD11b was tested for binding to 3141 FDA approved compounds. Initial screening of the compounds at 1 μM identified 30 compounds that bound with high affinity (see, FIGS. 1-3 which illustrate identification of carbamazepine, flufenamic acid and methyldopa, respectively).

Figure 4:
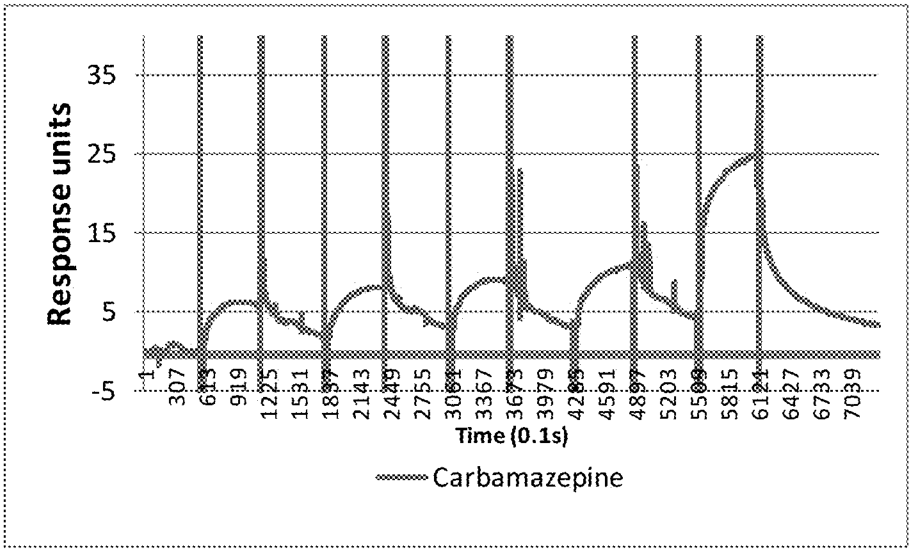
FIG. 4 is a graphical representation showing a single cycle kinetics curve of carbamazepine against human recombinant I-domain (rI-domain) of CD11b surface plasmon resonance assay. Maximum concentration was 10 nM with a 1:2 dilution down to 0.625 nM.
Figure 5:
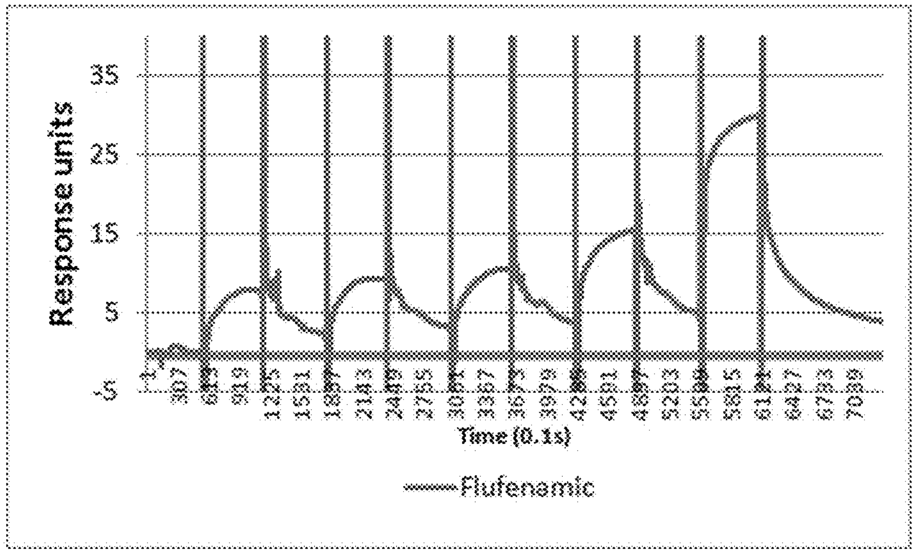
FIG. 5 is a graphical representation showing a single cycle kinetics curve of flufenamic acid against human rI-domain of CD11b surface plasmon resonance assay. Maximum concentration was 20 nM with a 1:2 dilution down to 1.25 nM.
Figure 6:
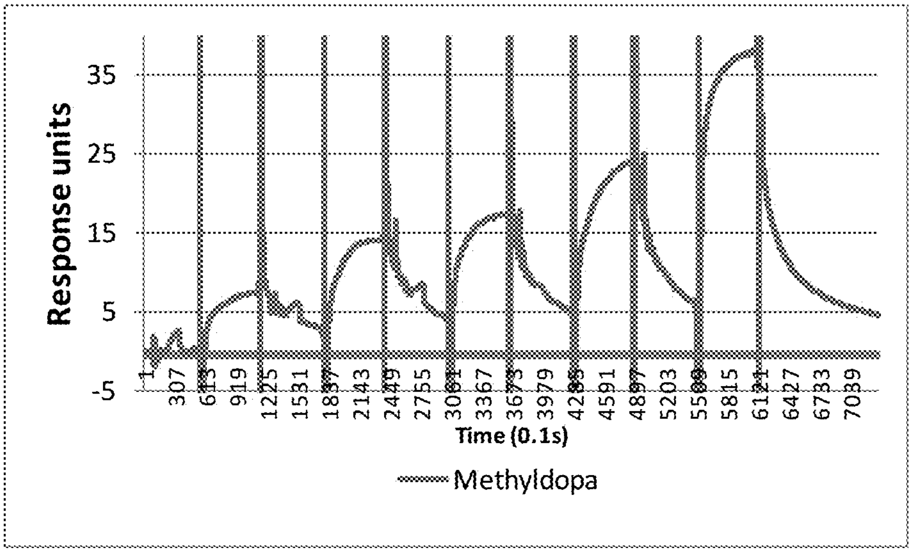
FIG. 6 is a graphical representation showing a single cycle kinetics curve of methyldopa against human rI-domain of CD11b surface plasmon resonance assay. Maximum concentration was 5 nM with a 1:2 dilution down to 0.3125 nM.

These 30 compounds were rescreened for binding affinity and ability to block *N. gonorrhoeae* MS11 wild type pilin and HIV from binding to human rI-domain in direct competition SPR experiments (see, FIGS. 4-6 which illustrate surface plasmon resonance curves for carbamazepine, flufenamic acid and methyldopa, respectively). Only 6 of the 30 compounds bound with high affinity and were able to completely block interactions with MS11 pilin. Only 4 of the 30 binding compounds were able to block HIV interaction with the human rI-domain. Only 3 of these blocking compounds (i.e., carbamazepine, flufenamic acid and methyldopa) met our criteria for current use and safety in humans. The 3 drugs shown in Table 1 can block interactions between CR3 or recombinant human I-domain and both *N. gonorrhoeae* MS11 pilin and HIV.

TABLE 1

COMPOUNDS FROM DRUG SCREEN WITH AFFINITY BELOW 1 μM THAT COULD BLOCK *NEISSERIA GONORRHOEAE* STRAIN MS11 PURIFIED PILIN AND/OR HIV INTERACTIONS WITH HUMAN RI-DOMAIN IN SURFACE PLASMON RESONANCE EXPERIMENTS.

| Compound | KD | Block MS11 pilin in SPR | Block HIV in SPR |
|---|---|---|---|
| CARBAMAZEPINE | 2.12 nM | Yes | Yes |
| METHYLDOPA | 1.01 nM | Yes | Yes |
| FLUFENAMIC ACID | 6.66 nM | Yes | Yes |

Tables 2 and 3 show the relative activity of the 3 compounds in inhibiting binding of human rI-domain to *Neisseria gonorrhoeae* MS11 pilin or primary T-cell derived WITO HIV, respectively.

TABLE 2

DRUGS BLOCK BINDING OF *NEISSERIA GONORRHOEAE* MS11 PILIN to RI-DOMAIN IN 1:1 COMPETITION ASSAYS.

| Drug name | Pilin RU | Drug RU | Pilin + Drug RU | % inhibition |
|---|---|---|---|---|
| CARBAMAZEPINE | 30.918 | 4.358 | 4.675 | 98.97% |
| FLUFENAMIC ACID | 30.918 | 4.627 | 10.872 | 79.80% |
| METHYLDOPA | 30.918 | 4.578 | 8.003 | 88.92% |

The data in Table 2 show that in 1:1 competition the drugs block I-domain binding to *Neisseria gonorrhoeae* MS11 pilin. Carbamazepine shows the best inhibition with ~99% blocking of Resonance Units (RU) accumulation observed. Drug or drug and pilin were flowed at 100 nM.

TABLE 3

DRUGS BLOCK BINDING OF PRIMARY T-CELL DERIVED WITO HIV TO RI-DOMAIN IN 1:1 COMPETITION ASSAYS.

| Drug name | Pilin RU | Drug RU | Pilin + Drug RU | % inhibition |
|---|---|---|---|---|
| CARBAMAZEPINE | 60.941 | 0.227 | 1.772 | 97.09% |
| FLUFENAMIC ACID | 60.941 | 0.473 | 8.857 | 85.47% |
| METHYLDOPA | 60.941 | 0.296 | 3.692 | 93.94% |

The data in Table 3 show that in 1:1 competition the drugs block I-domain binding to primary T-cell derived WITO HIV. Carbamazepine shows the best inhibition with ~97% blocking of RU accumulation observed. Drug or drug and rI-domain were flowed at 1 μM.

Materials and Methods

Reagents

PilE (Pilin Protein)

Purified pili from *N. gonorrhoeae* strain MS11 wild type and an isogenic MS11 strain containing a pglA::kan mutation described in Jennings et al (2011, *Cell Microbiol.* 13(6):885-96) was prepared based on previously described method Stimson et al (1995, *Mol Microbiol* 17:1201-1214), followed by further purification by electroelution of pilin monomers. In brief, the samples were separated on a 12% polyacrylamide gel and electro-eluted into SDS running buffer in a Mini Whole Gel Eluter (Bio-Rad) at 100 mA for 30 min. The different fractions were collected and 20 μL of each was analyzed using Western immunoblot analysis with the anti-pilin antibody to determine which fractions contained pilin, then purity assessed by 12% polyacrylamide gel and Coomassie straining. Purified pilin concentration was determined by BCA assay.

HIV: Purified HIV WITO Keele et al (2008, *Proc Natl Acad Sci USA.* 105(21):7552-7), Salazar-Gonzalez et al (2009, *J Exp. Med.* 206(6):1273-89) from HEK-293T cells that have been transfected with proviral DNA plasmid. WITO HIV were further amplified from infecting PHA activated peripheral blood mononuclear cells [PBMCs]) as previously described Jones et al (2010, *J Biol. Chem.* 285(24):18603-14), Garcia-Minambres et al (2017, *Immunol. Cell Biol.* 95(5):478-48). In brief, virus was purified from ultracentrifugation, and the quantity and infectivity of HIV were measured by HIV p24 protein ELISA and infection in TZM-bl reporter cells as previously described Jones et al (2010, supra), Garcia-Minambres et al (2017, supra). Purified viruses were then used for SPR blocking analyses.

Drug Libraries

A combination of two libraries, Microsource-CPOZ (2400 drugs) and ML Drug (741 drugs) libraries, including FDA approved drugs, were purchased from Compounds Australia (Compounds Australia; Griffith Institute for Drug Discovery, Griffith University, Building N75, Brisbane Innovation Park, Don Young Road, Nathan QLD 4111).

Drugs for Post-Screen Assays

All drugs for post-screening cellular assays (i.e., after Example 1) were obtained from SIGMA Aldrich (St Louis, Missouri): flufenamic acid, catalog number F9005-10G, carbamazepine, catalog number C4024-1G; methyldopa, catalog number 1426002-500MG.

Methods

Surface Plasmon Resonance (SPR)

SPR analyses were performed using a Biacore S200 System (GE Healthcare Life Sciences, Parramatta, NSW AUS). Samples were analyzed at 25° C. in phosphate buffered saline (PBS), at a flow rate of 10 μL/min, and by using single cycle kinetics. Human rI-domain as described in DuMont et al (2013, *Proc Nat Acad Sci.* 110(26):10794-9), mouse recombinant I-domain (mouse rI-domain) as described in DuMont et al (2013, *Proc Nat* Acad Sci. 110(26):10794-9), and human recombinant complement receptor 3 (rCR3; R&D Systems, Minneapolis, MN) were immobilized onto separate cells of a Series S CM5 sensor chip using a NHS capture kit (both from GE Healthcare Life Sciences) for purified pilin experiments using methods previously described in DuMont et al (2014, *Infect Immun.* 82:1268-76). Alternatively, for experiments in which free oligosaccharides with structures similar pilin-glycan were examined; human rI-domain and rCR3 were immobilized onto separate cells of a sensor chip. A blank immobilization was used as a control/reference (flow cell 1) on all chips. MS11 wild type pilin (binds rI-domain and rCR3) and MS11 pglA pilin (lacks terminal galactose, does not bind human rI-domain or rCR3) and two HIV strains, NL4-3 and NLAD8 were serially diluted from 2 μM to 0.125 μM in PBS. Positive control glycan ligands similar in structure to either the gonococcal pilin-linked glycan, α1l-3 galactobiose (Dextra Laboratories, Reading, UK, catalog number G203), or to HIV surface glycans, α1-3, α1-3, α1-6 mannopentaose (Dextra Laboratories, Reading, UK, catalog number M536), were serially diluted from 2 μM to 0.0078 μM in PBS, and included in the screening protocol to confirm the functionality of the immobilized human rI-domain, mouse rI-domain, and human rCR3 throughout the assay. Affinity data points were taken at 15 s after injection to avoid an artefactual signal resulting from bulk transport. SPR sensorgrams were analyzed using Biacore Evaluation software (GE Healthcare Life Sciences) to determine dissociation constants (i.e., $K_D$).

Repurposed Drug Screen Against Human rI-Domain of CD11b

Human rI-domain was immobilized onto a CM5 sensor chip with a blank control flow cell as described above. A combination of two libraries, including FDA approved drugs, Microsource-CPOZ (2400 drugs) and ML Drug (741 drugs), were purchased from Compounds Australia. Each drug was made up to 1 μM in 10% DMSO in a 384 well plate just prior to use in the Biacore S200 system. A new biosensor chip was made for each 384 well plate screened. A single concentration injection screen (yes/no) binding assay was performed. Binding was determined based on a response unit shift equal to the molecular weight corrected response units of the positive control glycan on the stability of binding phase of the dissociation cycle. “Hits” were rescreened across a concentration range of 1.6 nM to 1 μM to define the $K_D$ of the interaction. Any drug with a $K_D$ value >1 μM was discarded from the analysis. $K_D$ assays to determine high affinity interactions were further refined by using lower concentration ranges of compound to get the final affinity, as described in figure legends.

To determine if drugs with high affinity interactions with the human rI-domain could inhibit the interaction with MS11 pilin or HIV, competition assay between primary T-cell derived WITO HIV and *N. gonorrhoeae* MS11 pilin and the drugs were performed as described Mubaiwa et al (2017, Sci Rep. 7(1):5693). Competition analysis SPR of *N. gonorrhoeae* MS11 pilin and human rI-domain interaction was performed with human rI-domain immobilized on a CM5 sensor chip surface (low immobilization—~3500 RU compared to ~14000 RU for initial screening and $K_D$ calculations). *N. gonorrhoeae* MS11 purified pilin, drug or drug and pilin were flowed at 100 nM over the I-domain and the response units of the interactions were recorded.

For competition analysis SPR of the HIV interaction with human rI-domain, primary T-cell derived WITO HIV was immobilized on a Cl sensor chip surface. Human rI-domain, drug or drug and human rI-domain were flowed at 1 μM over the immobilized HIV and the response units of the interactions were recorded. Any drug that could not compete with the virus or pilin binding to the rI-domain was also discarded. Remaining drugs were evaluated for known safety in humans and known therapeutic concentrations to determine if the drug would be tested, and at what concentrations, in in vitro cell models. All SPR sensorgrams and results plots were analyzed with Biacore S200 Evaluation Software (GE Healthcare Life Sciences).

Example 2

Carbamazepine Blocks Adherence to Cho Cells

*N. gonorrhoeae* strain MS11gfp was used in drug blocking assays. The parent strain, MS11 Schoolnik et al (1984, *J Exp Med,* 159:1351-1370), Segal et al (1985, Cell 40: 293-300), was originally isolated from a patient with uncomplicated gonococcal cervicitis and is commonly used to study gonococcal pathogenesis. MS11gfp harbors the green fluorescent protein (GFP) expression plasmid, pCmGFP (GeneBank accession number FJ172221) Srikhanta et al (2009, *PLoS Pathog.* 5(4):e1000400) and, thus, expresses GFP Edwards et al (2000, *Infect Immun* 68(9):5354-63).

The ability of carbamazepine to block adherence of *N. gonorrhoeae* strain MS11gfp to CHO-neo or CHO-CR3 cells was evaluated using a fluorometric adherence assay. Assays were performed essentially as described by Jen et al (2013, *PLoS Pathog.* 9(5):e1003377). In this regard, CHO-neo or CHO-CR3 cells were seeded to a 96-well plate and allowed to grow to confluence. MS11gfp gonococci were then used to challenge (1 h) CHO cells simultaneously with, or without, various concentrations of carbamazepine (as noted). Fluorescence (485/528 nm) intensity, corresponding to bacterial adherence, was recorded using a Synergy HT Multi-mode Microplate Reader (BioTek Instruments, Winooski, VT USA). The assay was performed in triplicate on 3 separate occasions. A Kruskal-Wallis k-sample analysis of variance was used to determine the statistical significance of the calculated mean of bacterial adherence.

Figure 7:
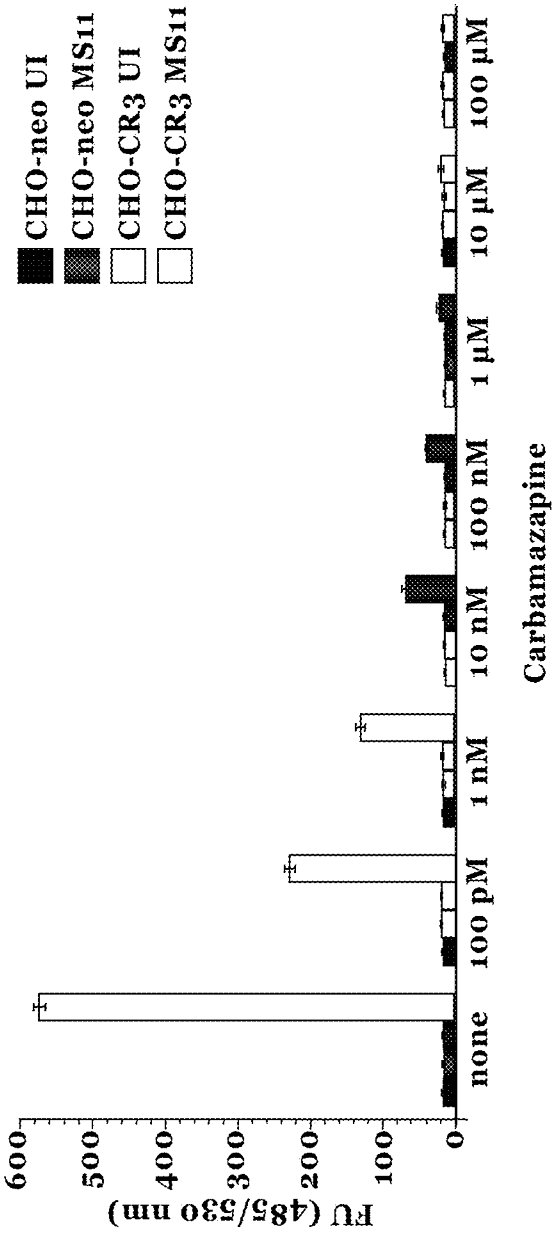
FIG. 7 is a graphical representation showing the effect of carbamazepine on gonococcal CHO cell adherence. A fluorometric adherence assay was used to determine the effect of carbamazepine on gonococcal adherence to CR3. Arbitrary fluorescence units (FU; y-axis), indicative of bacterial adherence, were recorded 1 h post-challenge of CHO-neo (control cells, non-CR3 expressing) and CHO-CR3 (CR3 expressing) cells with the green fluorescent protein (GFP)-expressing *N. gonorrhoeae* strain, MS11gfp. Data shown are the result of 3 separate assays performed in triplicate. A Student's t-test was used to determine the statistical significance of CR3-dependent bacterial adherence. A dose-dependent decrease in gonococcal adherence to CHO-CR3, but not CHO-neo, cells was observed in the presence of increasing concentrations of carbamazepine. The presence of 1 μM carbamazepine decreased gonococcal adherence to CHO- CR3 cells to a level that was not significantly different than that recorded for CHO-neo ($p \geq 0.057$) or uninfected cells ($p \geq 0.067$).

During natural infection, more than 92% of *N. gonorrhoeae* are associated with the female uterine cervix via an interaction with CR3 Edwards et al (2001, *Cell Microbiol.* 2001 3(9):611-22). The *N. gonorrhoeae*-CR3 interaction occurs solely through the I-domain, it requires gonococcal pilus Edwards et al (2002, *Cell Microbiol.* 4(9):571-84), and is mediated by the pilin-linked glycan Jennings et al (2011, *Cell Microbiol.* 13(6):885-96). Therefore, to examine the ability of carbamazepine to block the interaction of gonococci with the human rI-domain of CR3, the inventors performed fluorometric adherence assays. CR3-expressing (CHO-CR3) and non-expressing (CHO-neo) CHO cells, were seeded to microtiter plates, and gonococcal adherence was quantitated fluorometrically, as described previously Jen et al (2013, supra). A dose-dependent decrease in MS11gfp adherence to CHO-CR3, but not CHO-neo cells occurred when carbamazepine was included in the assay (FIG. 7). The presence of 1 μM carbamazepine decreased gonococcal adherence to CHO-CR3 cells to a level that was not significantly different than that recorded for CHO-neo cells ($p \geq 0.057$). Only background levels of fluorescence were recorded for assays performed using CHO-neo cells that were incubated with MS11gfp. Thus, these data demonstrate that, at micromolar concentrations, carbamazepine can block the adherence of gonococci to CR3-expressing cells.

Example 3

Methyldopa Blocks Adherence to Cho Cells

Figure 8:
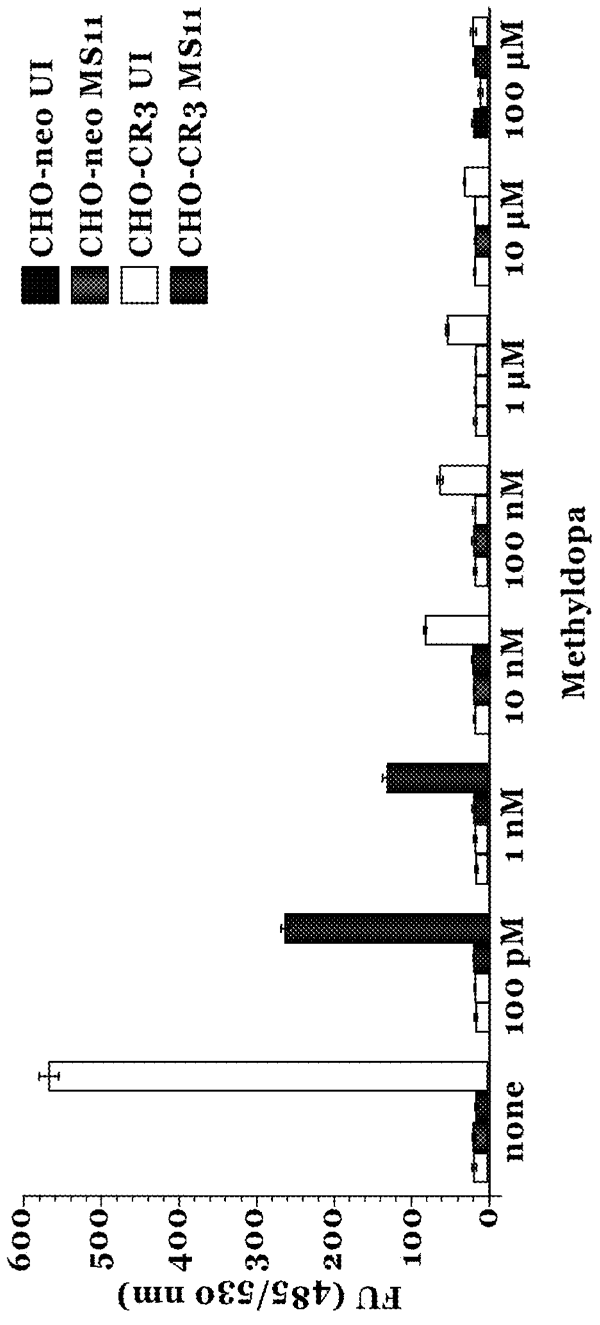
FIG. 8 is a graphical representation showing the effect of methyldopa on gonococcal CHO cell adherence. A fluorometric adherence assay was used to determine the effect of methyldopa on gonococcal adherence to CR3. Arbitrary fluorescence units (FU; y-axis), indicative of bacterial adherence, were recorded 1 h post-challenge of CHO-neo and CHO-CR3 cells with the green fluorescent protein (GFP)-expressing *N. gonorrhoeae* strain, MS11gfp. Data shown are the result of 3 separate assays performed in triplicate. A Student's t-test was used to determine the statistical significance of CR3-dependent bacterial adherence. A dose-dependent decrease in gonococcal adherence to CHO-CR3, but not CHO-neo, cells was observed in the presence of increasing concentrations of methyldopa. The presence of 100 μM methyldopa decreased gonococcal adherence to CHO-CR3 cells to a level that was not significantly different than that recorded for CHO-neo ($p \geq 0.23$) or uninfected cells ($p \geq 0.25$).

*N. gonorrhoeae* strain MS11gfp was used in drug blocking assays, as for Example 2. The ability of methyldopa to block adherence of *N. gonorrhoeae* strain MS11gfp to CHO-CR3 or CHO-neo cells was evaluated using a fluorometric adherence assay. Assays were performed essentially as described in Example 2. Notably, a dose-dependent decrease in MS11gfp adherence to CHO-CR3, but not CHO-neo cells occurred when methyldopa was included in the assay (FIG. 8). The presence of 100 μM methyldopa decreased gonococcal adherence to CHO-CR3 cells to a level that was not significantly different than that recorded for CHO-neo cells (p 0.23). Only background levels of fluorescence were recorded for assays performed using CHO-neo cells that were incubated with MS11gfp. Thus, these data demonstrate that, at micromolar concentrations, methyldopa can block the adherence of gonococci to CR3-expressing cells.

Example 4

Flufenamic Acid Blocks Adherence to Cho Cells

Figure 9:
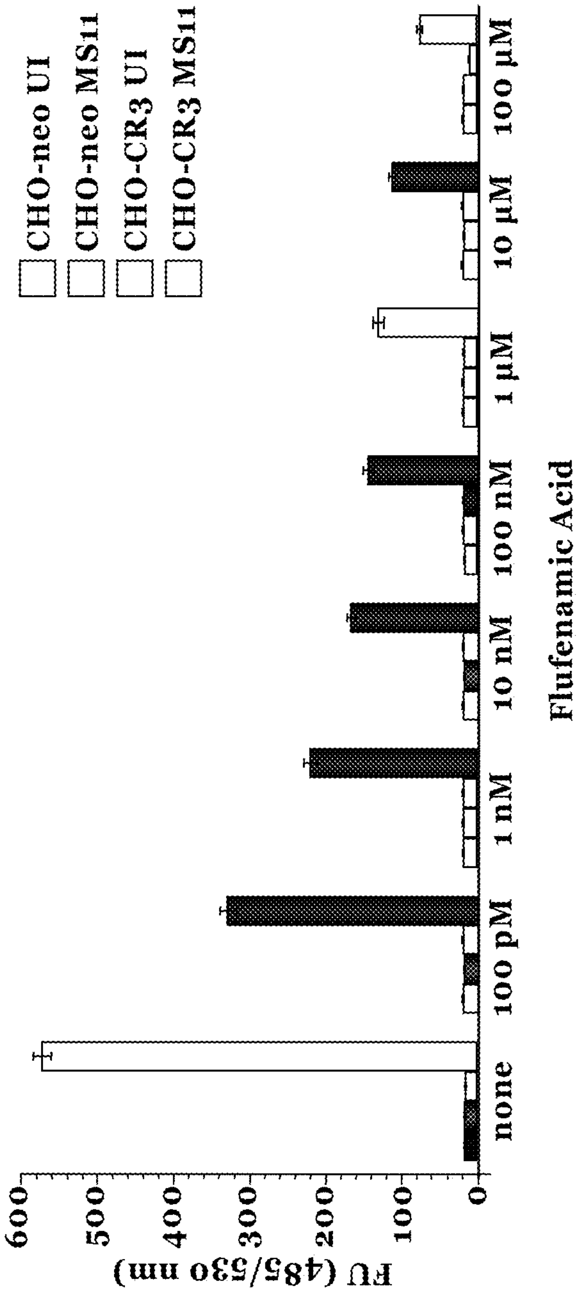
FIG. 9 is a graphical representation showing the effect of flufenamic acid on gonococcal CHO cell adherence. A fluorometric adherence assay was used to determine the effect of flufenamic acid on gonococcal adherence to CR3. Arbitrary fluorescence units (FU; y-axis), indicative of bacterial adherence, were recorded 1 h post-challenge of CHO-neo and CHO-CR3 cells with the green fluorescent protein (GFP)-expressing *N. gonorrhoeae* strain, MS11gfp. Data shown are the result of 3 separate assays performed in triplicate. A Student's t-test was used to determine the statistical significance of CR3-dependent bacterial adherence. A dose-dependent decrease in gonococcal adherence to CHO-CR3, but not CHO-neo, cells was observed in the presence of increasing concentrations flufenamic acid. Greater than 86% blocking of the adherence of gonococci to CR3 occurred in the presence of 100 μM flufenamic acid.

*N. gonorrhoeae* strain MS11gfp was used in drug blocking assays, as for Example 2. The ability of flufenamic acid to block adherence of *N. gonorrhoeae* strain MS11gfp to CHO-CR3 or CHO-neo cells was evaluated using a fluorometric adherence assay. Assays were performed essentially as described in Example 2. Inspection of FIG. 9 shows that a dose-dependent decrease in MS11gfp adherence to CHO-CR3, but not CHO-neo cells occurred when flufenamic acid was included in the assay. Only background levels of fluorescence were recorded for assays performed using CHO-neo cells that were incubated with MS11gfp. Thus, these data demonstrate that, at micromolar concentrations, flufenamic acid can block the adherence of gonococci to CR3-expressing cells.

Example 5

Carbamazepine Blocks Adherence to Human, Primary Cervical Epithelial (PEX) Cells During natural infection, more than 92% of *N. gonorrhoeae* are associated with the female uterine cervix via an interaction with CR3 (Edwards et al., 2001, *Cell Microbiol.* 2001 3(9):611-22). The *N. gonorrhoeae*-CR3 interaction occurs solely through the I-domain, it requires gonococcal pilus (Edwards et al., 2002. *Cell Microbiol.* 4(9):571-84), and is mediated by the pilin-linked glycan (Jennings et al 2011. *Cell Microbiol.* 13(6):885-96). Therefore, the present inventors examined the ability of carbamazepine to block the interaction of gonococci with the CR3 I-domain on cervical mucosa.

Briefly, six *N. gonorrhoeae* strains were used in the experiments. These included the laboratory strain, MS11; the low-passage isolates, 1291, UT38097, LT38885, PID-26, and SK92-679; all of which were transformed with the green fluorescent protein (GFP) expression plasmid, pCmGFP (GenBank accession number FJ172221) Srikhanta et al (2009, *PLoS Pathog.* 5(4):e1000400) and, thus, expressed GFP Edwards et al (2000, *Infect Immun* 68(9): 5354-63). These strains exhibit diverse pili amino acid sequences and pilin glycosylation structures. The ability of carbamazepine to block the adherence of *N. gonorrhoeae* to human, primary cervical epithelial (PEX) cells was evaluated using a fluorometric adherence assay. Assays were performed essentially as described by Jen et al (2013, supra). In this regard, PEX cells were seeded to a 96-well plate and allowed to grow to confluence. Gonococci were then used to challenge (1 h) PEX cells simultaneously with, or without, various concentrations of carbamazepine (100 μM, 10 nM, 1 μM, or 100 μM, as noted) or 1% DMSO (vehicle control). Uninfected PEX cells treated with 1% DMSO served as a control for background fluorescence. Fluorescence (485/528 nm) intensity, corresponding to bacterial adherence, was recorded using a Synergy HT Multi-mode Microplate Reader (BioTek Instruments, Winooski, VT USA). The assay was performed in triplicate on 3 separate occasions. A Student's t-test was used to determine the statistical significance of the calculated mean of bacterial adherence.

Figure 10:
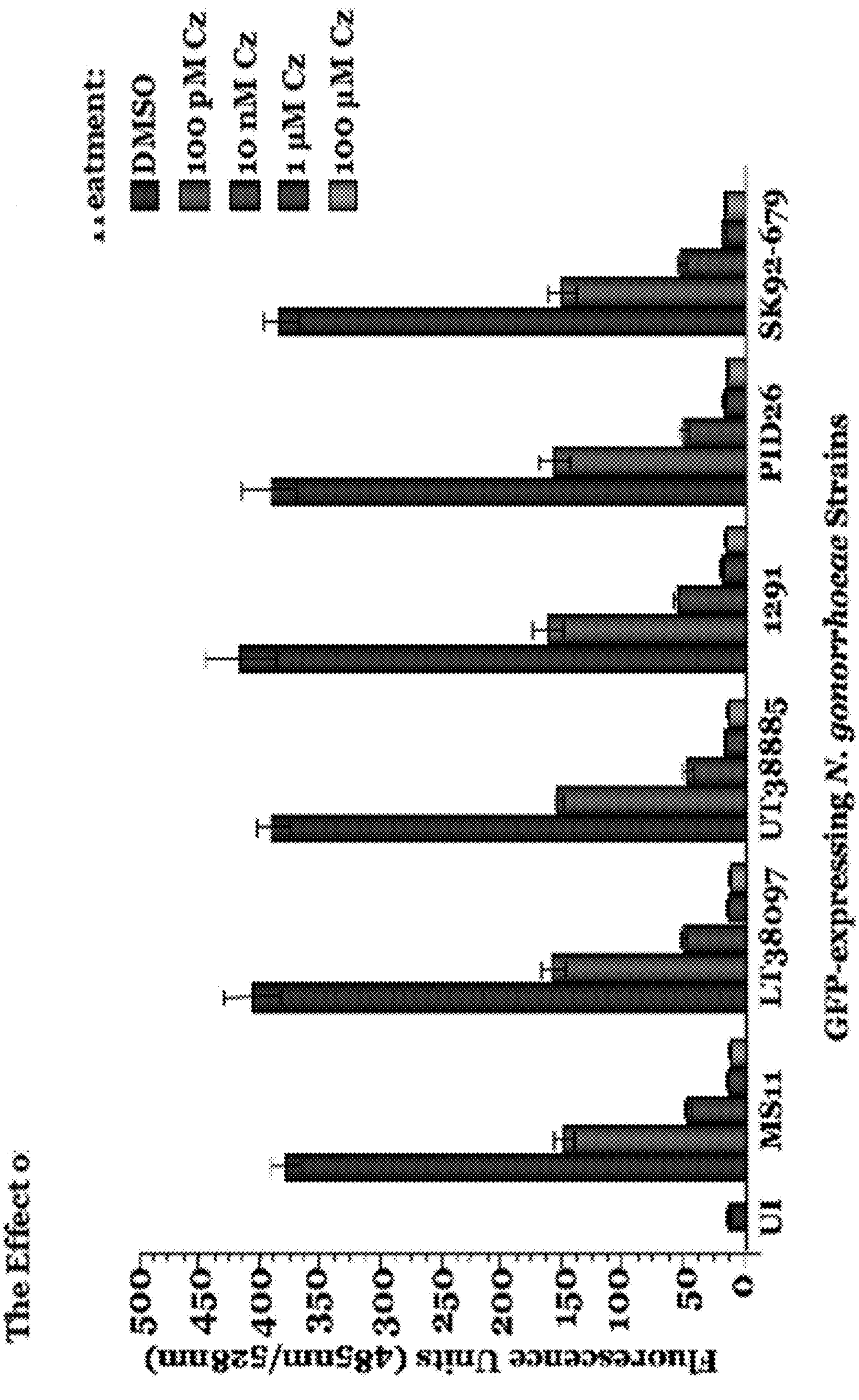
FIG. 10 is a graphical representation showing the effect of carbamazepine on *N. gonorrhoeae* adherence to PEX cells. A fluorometric adherence assay was used to determine the effect of carbamazepine on gonococcal adherence to CR3. Arbitrary fluorescence units (y-axis), indicative of bacterial adherence, were recorded at 1 h post-challenge of primary human cervical epithelial (i.e., PEX) cells with *N. gonorrhoeae* strains that expressed green fluorescent protein (GFP). Data shown are the result of 3 separate assays performed in triplicate. A Student's t-test was used to determine the statistical significance of CR3-dependent bacterial adherence. A significant ($p^3$ 0.0001) dose-dependent decrease in gonococcal adherence to PEX cells was observed for all strains tested in the presence of increasing concentrations carbamazepine when compared to infections treated with DMSO (vehicle control). In this regard, greater than 95% inhibition of adherence occurred in the presence of 1 μM carbamazepine for all strains tested.

The results presented in FIG. 10 reveal that a dose-dependent decrease in adherence to PEX cells occurred for all strains tested when carbamazepine was included in the assay. In this regard, greater than 95% inhibition of adherence occurred in the presence of 1 μM carbamazepine for all strains tested. Thus, these data demonstrate that carbamazepine blocks the adherence of gonococci to CR3-expressing cells.

Example 6

Methyldopa Blocks Adherence to Human PEX Cells

Figure 11:
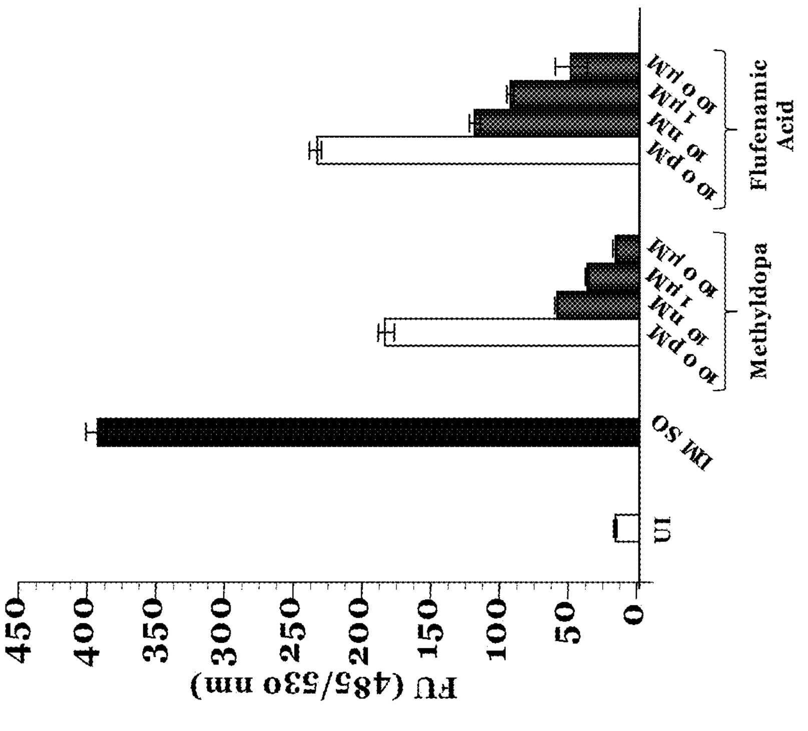
FIG. 11 is a graphical representation showing the effect of methyldopa and flufenamic acid on *N. gonorrhoeae* strain MS11 adherence to PEX cells. A fluorometric adherence assay was used to determine the effect of methyldopa and flufenamic acid on gonococcal adherence to CR3. Arbitrary fluorescence units (FU, y-axis), indicative of bacterial adherence, were recorded at 1 h post-challenge of PEX cells with the green fluorescent protein (GFP)-expressing *N. gonorrhoeae* strain, MS11gfp. Data shown are the result of 3 separate assays performed in triplicate. A Student's t-test was used to determine the statistical significance of CR3-dependent bacterial adherence. A significant ($p \leq 0.0001$) dose-dependent decrease in gonococcal adherence to PEX cells was observed in the presence of increasing concentrations of both methyldopa and flufenamic acid. Of note is that the presence of 100 μM methyldopa decreased gonococcal adherence to PEX cells to a level that was not significantly ($p \geq 0.234$) different than that recorded for uninfected cells.
Figure 12:
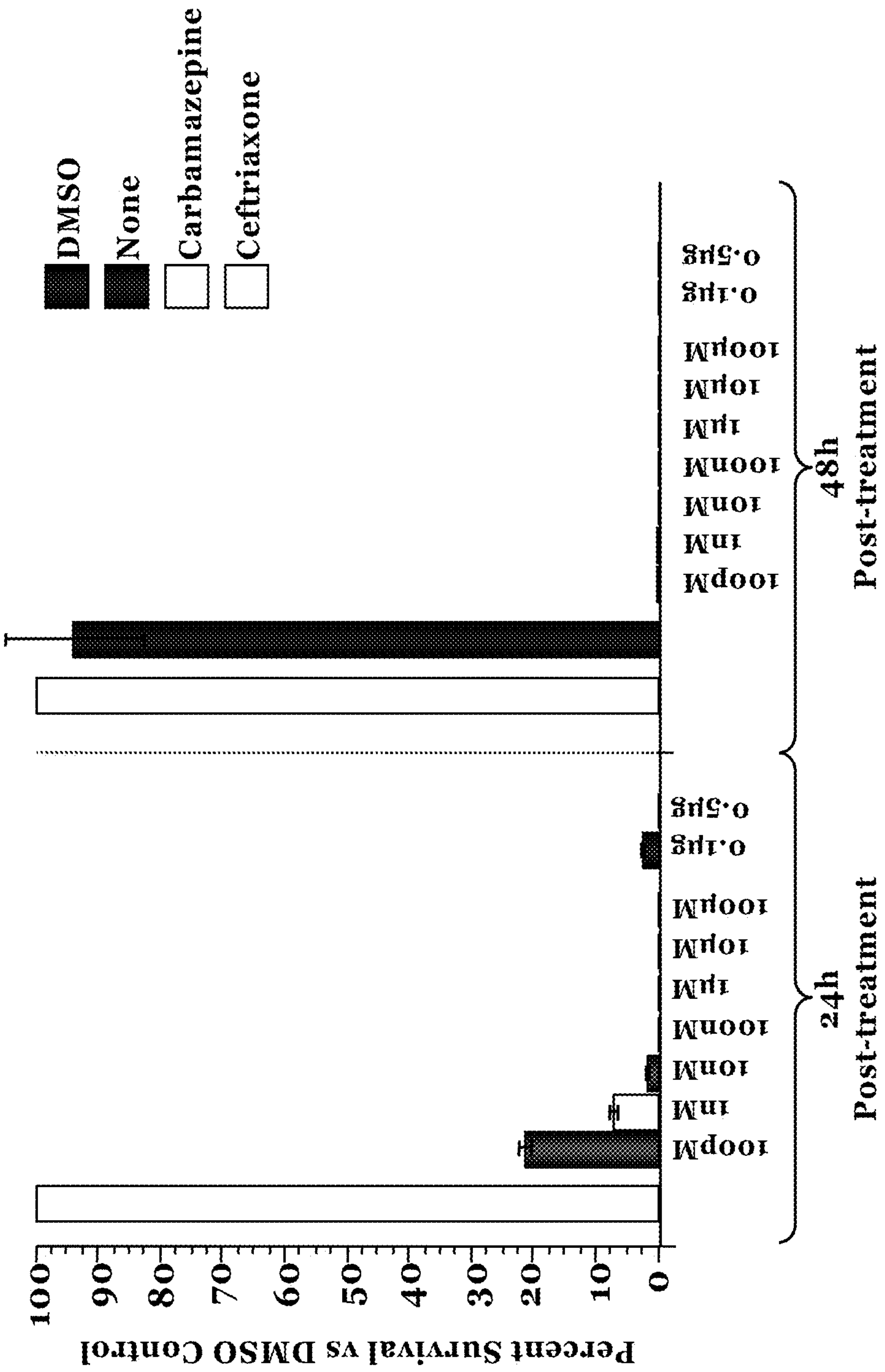
FIG. 12 is a graphical representation showing the effect of carbamazepine dose on the treatment of PEX cells infected with *N. gonorrhoeae* strain MS11. To establish infection, PEX cells were challenged with *N. gonorrhoeae* strain MS11 for 90 min. Infections were then allowed to proceed for an additional 24 h or 48 h in the presence or absence of DMSO (1% vehicle control), carbamazepine (CZ), or ceftriaxone (positive control), as noted. The percentage of *N. gonorrhoeae* that survived carbamazepine or ceftriaxone treatment (y-axis) was determined as a function of bacteria that survived DMSO treatment at the same time point (set to 100%). Data shown are the result of 3 separate assays performed in triplicate. A Kruskal-Wallis k-sample analysis of variance was used to determine the statistical significance of bacterial survival. At all concentrations tested, carbamazepine treatment resulted in a significant decrease ($p \leq 0.0001$) in viable *N. gonorrhoeae*. Greater than 98% gonococcal killing occurred with carbamazepine concentrations greater than, or equal to, 10 nM.

The ability of methyldopa to block adherence of *N. gonorrhoeae* strain MS11gfp to human, primary cervical epithelial cells was evaluated using a fluorometric adherence assay, as described in Example 5. Inspection of FIG. 11 reveals that a dose-dependent decrease in MS11gfp adherence to PEX cells occurred when methyldopa was included in the assay. In this regard, approximately 85% inhibition of adherence occurred in the presence of 10 nM methyldopa. Data obtained with the use of 1 μM methyldopa were not significantly ($p \geq 0.234$) different than those obtained for vehicle (DMSO)-treated, uninfected PEX cells. Thus, these data demonstrate that methyldopa blocks the adherence of gonococci to CR3-expressing cells.

Example 7

Flufenamic Acid Blocks Adherence to Human PEX Cells

The ability of flufenamic acid to block adherence of *N. gonorrhoeae* strain MS11gfp to human, primary cervical epithelial cells was evaluated using a fluorometric adherence assay, as described in Example 5. The results shown in FIG.

11 show that a dose-dependent decrease in MS11gfp adherence to PEX cells occurred when flufenamic acid was included in the assay. In this regard, approximately 70% inhibition of adherence occurred in the presence of 10 nM flufenamic acid. Thus, these data demonstrate that methyldopa blocks the adherence of gonococci to CR3-expressing cells.

Example 8

Carbamazepine can Treat an Established *N. gonorrhoeae* Infection in PEX Cells

Figure 14:
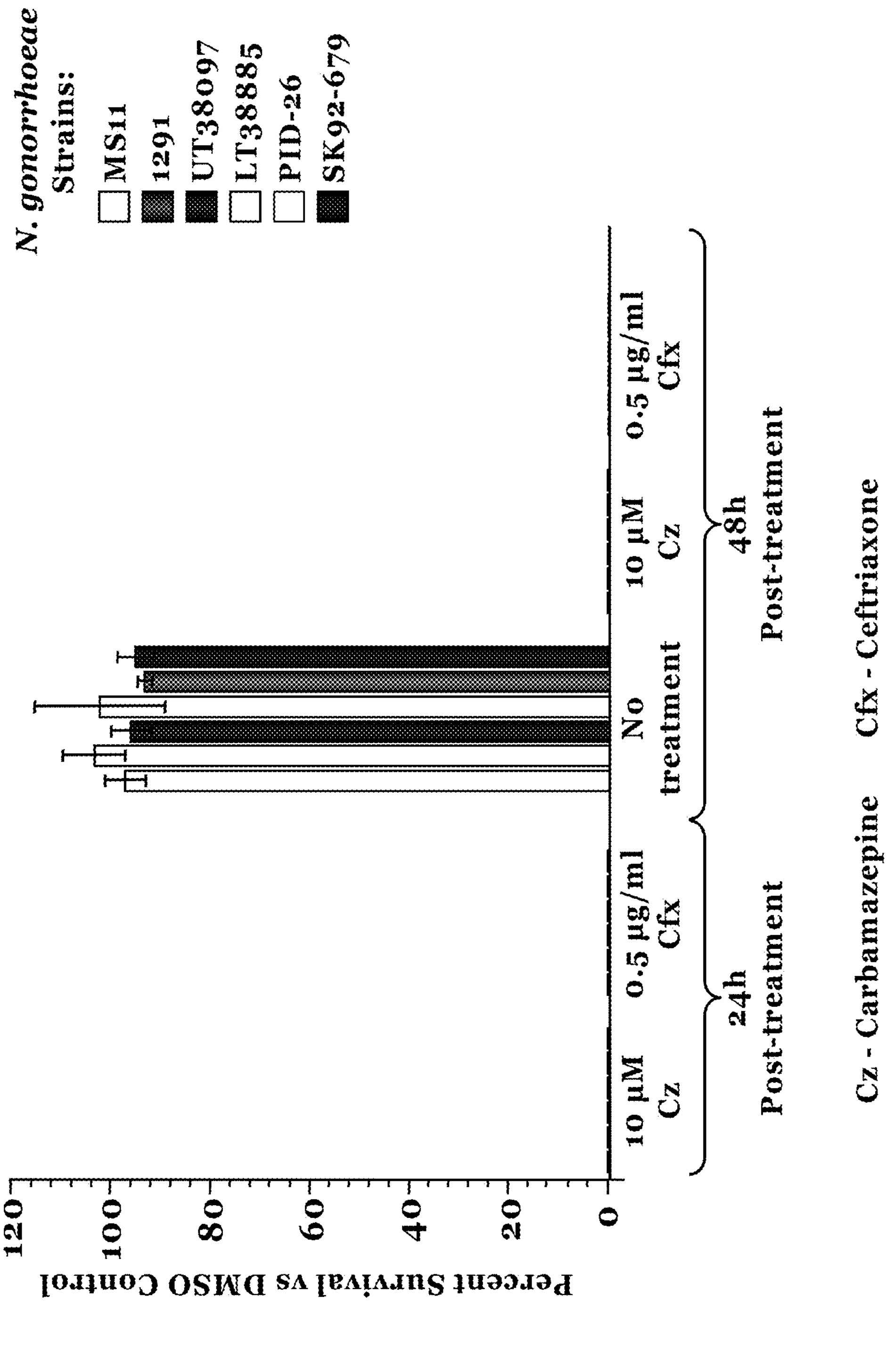
FIG. 14 is a graphical representation showing the effect of a single dose carbamazepine treatment of PEX cells infected with low-passage *N. gonorrhoeae* isolates. To establish infection, PEX cells were challenged with *N. gonorrhoeae* for 90 min using the noted low-passage isolates. Infections were then allowed to proceed for an additional 24 h or 48 h in the presence or absence of DMSO (1%, vehicle control), carbamazepine (10 μM, CZ), or ceftriaxone (0.5 μg/mL, positive control). The percentage of *N. gonorrhoeae* that survived carbamazepine, ceftriaxone, or no treatment (y-axis) was determined as a function of bacteria that survived DMSO treatment at the same time point (set to 100%, not shown). Data shown are the result of 3 separate assays performed in triplicate. A Kruskal-Wallis k-sample analysis of variance was used to determine the statistical significance of bacterial survival. Carbamazepine treatment resulted in a significant decrease ($p \leq 0.0001$) in the ability of each strain tested to survive. Greater than 99% gonococcal killing occurred with a 24 h, 10 μM carbamazepine treatment.
Figure 15:
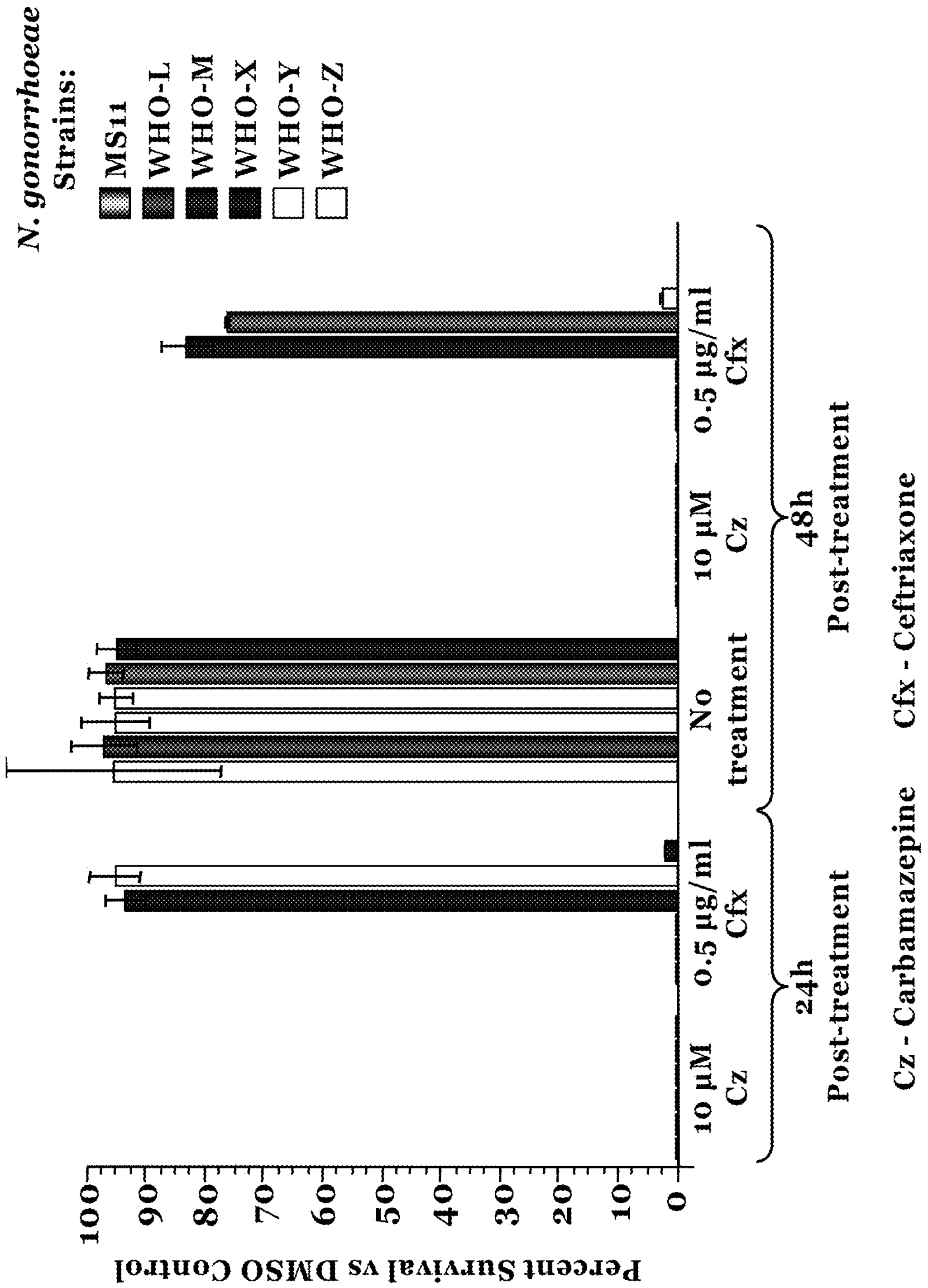
FIG. 15 is a graphical representation showing the effect of a single dose carbamazepine treatment of PEX cells infected with multidrug-resistant *N. gonorrhoeae*. PEX cells were challenged with the noted multidrug-resistant *N. gonorrhoeae* strains for 90 min to establish infection. Infections were then allowed to proceed for an additional 24 h or 48 h in the presence or absence of DMSO (1%, vehicle control), carbamazepine (10 μM, CZ), or ceftriaxone (0.5 μg/mL, positive control). The percentage of *N. gonorrhoeae* that survived carbamazepine, ceftriaxone, or no treatment (y-axis) was determined as a function of bacteria that survived DMSO treatment at the same time point (set to 100%, not shown). Data shown are the result of 3 separate assays performed in triplicate. A Kruskal-Wallis k-sample analysis of variance was used to determine the statistical significance of bacterial survival. Carbamazepine treatment resulted in a significant decrease ($p \leq 0.0001$) in the ability of each multidrug-resistant strain tested to survive. Greater than 99% gonococcal killing occurred with a 24 h, 10 μM carbamazepine treatment.

*N. gonorrhoeae* strains used in survival assays included MS11 Schoolnik et al (1984, supra), Segal et al (1985, supra) and 1291 Apicella et al (1974, *J. Infect Dis.* 130(6):619-25), Dudas and Apicella (1988, *Infect Immun.* 56(2):499-504), which are commonly used to study gonococcal pathogenesis. Also examined were a panel of low-passage clinical isolates (FIG. 14; i.e., *N. gonorrhoeae* strains LT38097, UT38885, PID-26, and SK92-679). Strains 1291 and LT38097 are male urethral isolates; strains MS11 and UT38885 were obtained from women with uncomplicated gonococcal cervicitis, strain PID-26 was obtained from a patient with pelvic inflammatory disease; and strain SK92-679 is a blood isolate from a patient with disseminated infection. Antibiotic-resistant *N. gonorrhoeae* strains tested were obtained from Public Health England and comprised WHO-L, WHO-M, WHO-X (H041), WHO-Y (F89), and WHO-Z (A8806), see FIG. 15. For use, bacteria were harvested from overnight (37° C., 5% $CO_2$), GC-IsoVitaleX agar plate cultures and enumerated spectrophotometrically, as previously described Edwards et al (2000, *Infect Immun* 68(9):5354-63). Infection studies were performed using a multiplicity of infection of 100 Edwards et al (2000, *Infect Immun* 68(9):5354-63).

Figure 13:
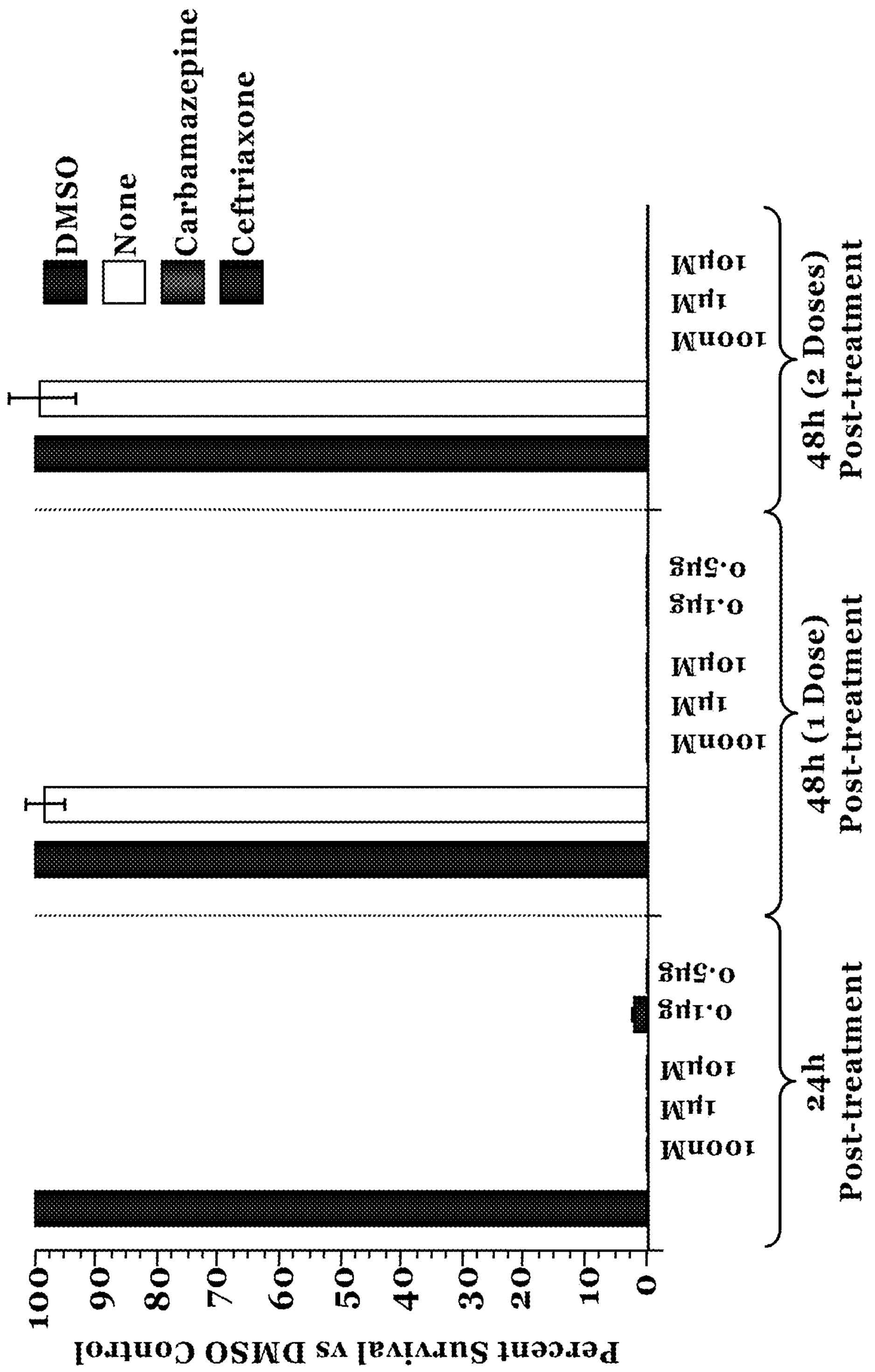
FIG. 13 is a graphical representation showing the effect of a two dose carbamazepine treatment of PEX cells infected with *N. gonorrhoeae* strain MS11. PEX cells were challenged with *N. gonorrhoeae* strain MS11 for 90 min to establish infection. Infections were then allowed to proceed for an additional 24 h or 48 h (48 h-1 dose) in the presence or absence of DMSO (1% vehicle control), carbamazepine (CZ), or ceftriaxone (positive control), as noted. Where indicated, a second dose of carbamazepine (at the noted concentration) was added at 24 h post-infection, and infections were allowed to proceed for an additional 24 h (48 h-2 doses). The percentage of *N. gonorrhoeae* that survived carbamazepine or ceftriaxone treatment (y-axis) was determined as a function of bacteria that survived DMSO treatment at the same time point (set to 100%). Data shown are the result of 3 separate assays performed in triplicate. A Kruskal-Wallis k-sample analysis of variance was used to determine the statistical significance of bacterial survival. At each time point, and for all concentrations tested, carbamazepine treatment resulted in a significant decrease ($p \leq 0.0001$) in viable *N. gonorrhoeae*. Greater than 99% gonococcal killing occurred by 24 h with a single, 100 nM dose of carbamazepine; greater than 99.95% killing of gonococci had occurred by 48 h of infection with 2-100 nM doses of carbamazepine, applied 24 h apart.
Figure 16:
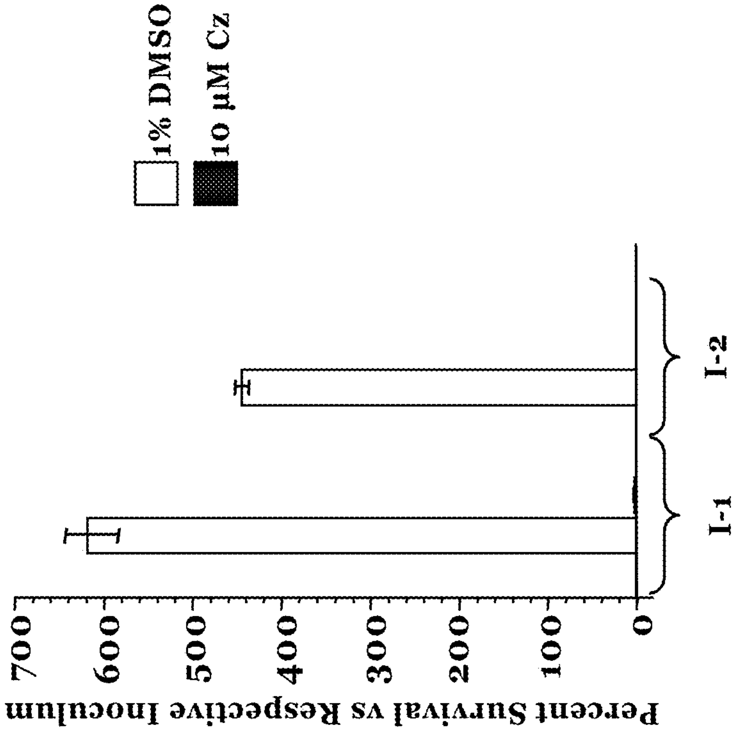
FIG. 16 is a graphical representation showing a *N. gonorrhoeae* strain, MS11, carbamazepine sequential infection cure assay. To determine whether the observed small percentage of *N. gonorrhoeae* that survive a 24 h treatment had developed resistance to carbamazepine treatment of PEX cells, sequential infection assays were conducted. PEX cells were challenged with *N. gonorrhoeae* strain MS11 for 90 min to establish infection and then treated with 1% DMSO (vehicle control) or 10 μM carbamazepine (Cz). Infections were allowed to proceed for 24 h, after which PEX cells were lysed and viable gonococci were enumerated by plating serial dilutions of the PEX cell lysate (infection 1; I-1). These "break-through" gonococcal colonies were harvested and then used as the inocula for new, 24 h, infection assays (infection 2; 1-2). The y-axis shows the percentage of viable colony forming units as determined as a function of each respective infection inoculum. For both infections (infection 1 and infection 2), a significant ($p \leq 0.0001$) decrease in gonococcal survival occurred in the presence of carbamazepine when compared to infections treated with DMSO, and 100% gonococcal killing was observed following the second infection. Thus, these sequential infection studies revealed that the initial survivor, "break-through", population of gonococci were no more resistant to carbamazepine treatment of PEX cells than the initial infection inoculum. All assays were performed in triplicate on 3 separate occasions with *N. gonorrhoeae* strain MS11. A Kruskal-Wallis k-sample analysis of variance was used to determine the statistical significance of bacterial survival.

PEX cells were challenged with the noted *N. gonorrhoeae* strains for 90 min. For single dose survival assays, the infection medium was then removed, cells were rinsed thrice, and fresh medium containing 1% DMSO (vehicle control), carbamazepine (100 μM-100 μM, as noted), or ceftriaxone (0.1 μg/mL or 0.5 μg/mL, positive control) was added. Infections were then allowed to proceed for an additional 24 h or 48 h. At the indicated times post-treatment, the infection medium was removed, the PEX cell monolayers were rinsed thrice, lysed, and viable *N. gonorrhoeae* were enumerated by counting colony forming units after plating serial dilutions of the PEX cell lysates (for example see 12). In some experiments (i.e., two dose survival assays for example see FIG. 13), a second dose of carbamazepine was added at 24 hours-post addition of the first carbamazepine dose. Infections were then allowed to proceed for an additional 24 h before plating the PEX cell lysate, as above. For either assay, the percentage of *N. gonorrhoeae* that survived carbamazepine or antibiotic treatment was determined as a function of bacteria that survived DMSO (vehicle control) treatment (set to 100%). In the treatment assays greater than 99.95% killing of gonococci occurs by 24 hours at carbamazepine concentrations of 10 μM or higher. To investigate whether the small percentage of the surviving bacterial cells have developed resistance to the treatment, sequential infection assays were conducted. Bacteria were harvested from the CFU count plates and then used to inoculate a new assay. These sequential assay studies revealed that the survivor population of bacteria were no more resistant to the treatment than the initial inocula (see FIG. 16). All assays were performed in triplicate on 3 separate occasions with the noted bacterial strains. A Kruskal-Wallis k-sample analysis of variance was used to determine the statistical significance of bacterial survival.

The results presented in FIGS. 12 to 16 demonstrate that carbamazepine can treat PEX cells that have an established infection with a range of *N. gonorrhoeae* strains including multidrug resistant strains.

Example 9

HIV Binds to CHO Cells in a CR3-Dependent Fashion, and Carbamazepine Can Block HIV Binding to CR3 on Cho-CR3 Cells HIV strains NL4-3 and NLAD8 were used in drug blocking of adherence to CHO cells.

SPR studies indicated that the human rI-domain of CR3 can bind to HIV. To test the ability of HIV to bind to CHO cells in a CR3 dependent fashion, and to test the ability of carbamazepine to block adherence of HIV to CHO-CR3 or CHO-neo cells, a fluorometric adherence assay was used, essentially as described by Jen et al (2013, supra). In this regard, CHO-neo or CHO-CR3 cells were seeded to a 96-well plate and allowed to grow to confluence. Fluorescently labelled HIV (10 ng of p24 HIV capsid protein equivalent of HIV in 100 μL of F12 culture media) were then used to challenge (2 h) CHO cells simultaneously with, or without, various concentrations of carbamazepine (as noted). Fluorescence (485/528 nm) intensity, corresponding to HIV cell adherence, was recorded using a Synergy HT Multi-mode Microplate Reader (BioTek Instruments, Winooski, VT USA). The assay was performed in triplicate on 3 separate occasions. A Kruskal-Wallis k-sample analysis of variance was used to determine the statistical significance of the calculated mean of viral-cell adherence.

Figure 17:
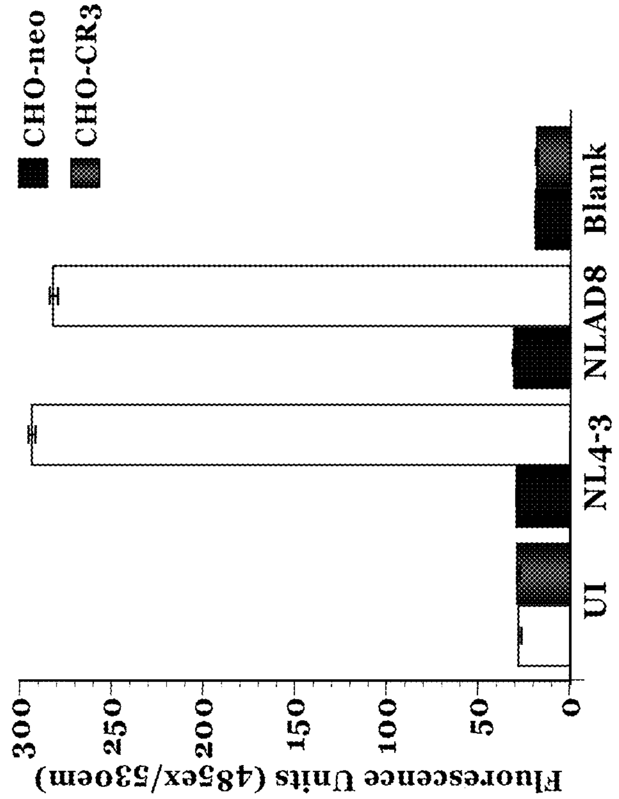
FIG. 17 is a graphical representation depicting the CR3-dependent HIV Adherence to CHO Cells. A fluorometric adherence assay was used to determine the ability of HIV to bind to CHO cells in a CR3-dependent fashion. Arbitrary fluorescence units (y-axis), indicative of adherence, were recorded at 2 h post-challenge of CHO-neo and CHO-CR3 cells with fluorescently labelled HIV (10 ng of p24 HIV capsid protein equivalent in 100 μL of F12 culture media). Two HIV strains were tested, NLAD8 (also known as NL4-3 ADS) and NL4-3, each of which bound to CR3-expressing, but non-CR3-expressing, CHO cells. In this regard, fluorescence recorded for CHO-neo cells that were challenged with HIV were not significantly different ($p \geq 0.12$) from uninfected cells. Data shown are the result of 3 separate assays performed in triplicate. A Student's t-test was used to determine the statistical significance of CR3-dependent HIV adherence to CHO cells.

Fluorometric adherence assays were carried out with HIV strains NL4-3 and NLAD8. CR3-expressing (CHO-CR3) and non-expressing (CHO-neo) CHO cells, were seeded to microtiter plates, and gonococcal adherence was quantitated fluorometrically, as described by Jen et al. (2013, supra). Adherence of both HIV strains to CHO cells was only observed when CR3 was present, expressed on the CHO-CR3 cells (FIG. 17), as there was no statistically significant difference between adherence to CHO-neo cells and the uninfected control (NL4-3, P 0.37; NLAD8 P=0.12).

Figure 18:
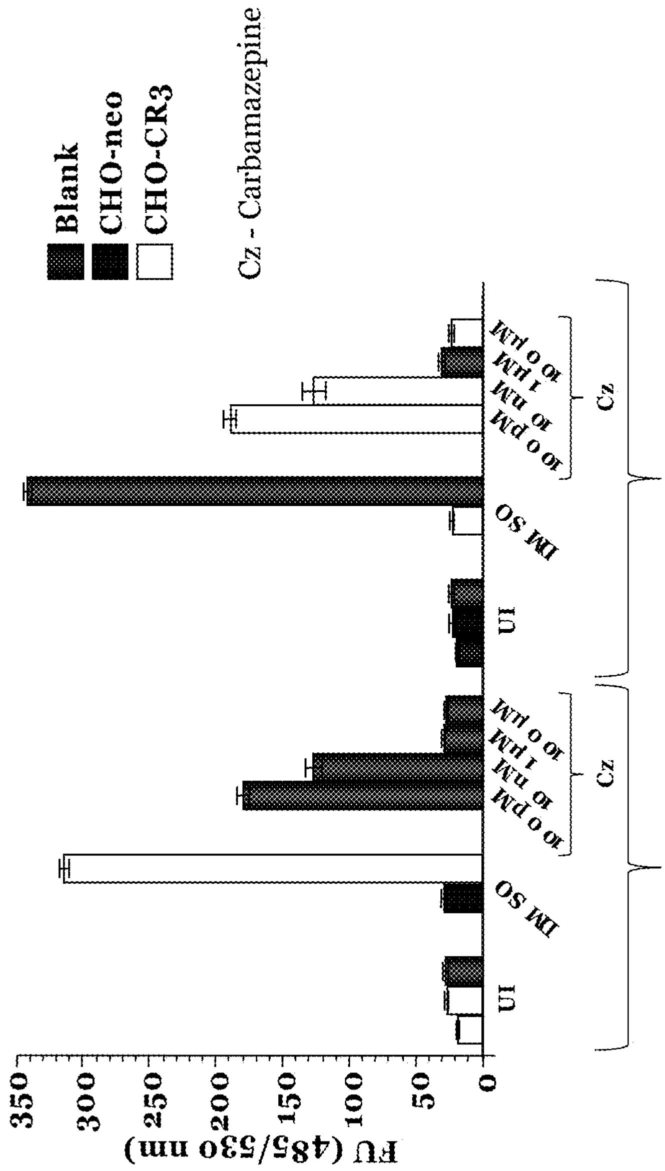
FIG. 18 is a graphical representation showing the effect of carbamazepine on HIV CHO Cell Adherence. A fluorometric adherence assay was used to determine the effect of carbamazepine on HIV adherence to CR3. Arbitrary fluorescence units (y-axis), indicative of adherence, were recorded 2 h post-challenge of CHO-neo and CHO-CR3 cells with fluorescently labelled HIV (10 ng of p24 HIV capsid protein equivalent in 100 μL of F12 culture media) strains, NLAD8 and NL4-3. Data shown are the result of 3 separate assays performed in triplicate. A Student's t-test was used to determine the statistical significance of CR3-dependent HIV adherence. A significant ($p \leq 0.0001$) dose-dependent decrease in HIV adherence to CHO-CR3, but not CHO-neo, cells was observed for both strains in the presence of increasing concentrations carbamazepine. The presence of 1 μM carbamazepine decreased HIV adherence to CHO-CR3 cells to a level that was not significantly different than that recorded for CHO-neo cells ($p \geq 0.061$ for NL4-3; $p \geq 0.8$ for NLAD8) or uninfected cells ($p \geq 0.067$).

Having established the CR3-dependent binding of HIV to CHO cells, the inventors next examined the ability of carbamazepine to block the interaction of HIV strains NL4-3 and NLAD8 with the CR3 I-domain using fluorometric adherence assays. CR3-expressing (CHO-CR3) and non-expressing (CHO-neo) CHO cells, were seeded to microtiter plates, and HIV adherence was quantitated fluorometrically, as described by Jen et al. (2013, supra). A dose-dependent decrease in HIV strains NL4-3 and NLAD8 cell adherence with CHO-CR3, but not CHO-neo cells occurred when carbamazepine was included in the assay (see, FIG. 18). The presence of 1 μM carbamazepine decreased NL4-3 and NLAD8 cell adherence to CHO-CR3 cells to a level that was not significantly different than that recorded for CHO-neo cells ($p \geq 0.061$). Only background levels of fluorescence were recorded for assays performed using CHO-neo cells that were incubated with NL4-3 and NLAD8. Thus, these data demonstrate that, at 1 μM concentrations, carbamazepine can block NL4-3 and NLAD8 cell adherence to CR3-expressing cells.

Example 10

Carbamazepine Blocks Adherence of HIV to PEX Cells

HIV strains NL4-3 and NLAD8 were used in drug blocking of adherence to PEX cells.

The ability of carbamazepine to block adherence of HIV to human PEX cells was evaluated using a fluorometric adherence assay, essentially as described by Jen et al. (2013, supra). In this regard, PEX cells were seeded to a 96-well plate and allowed to grow to confluence. Fluorescently labelled HIV (10 ng of p24 HIV capsid protein equivalent of HIV in 100 μL of F12 culture media) were then used to challenge (2 h) PEX cells simultaneously with, or without, various concentrations of carbamazepine (as noted). Fluorescence (485/528 nm) intensity, corresponding to HIV cell adherence, was recorded using a Synergy HT Multi-mode Microplate Reader (BioTek Instruments, Winooski, VT USA). The assay was performed in triplicate on 3 separate occasions. A Kruskal-Wallis k-sample analysis of variance was used to determine the statistical significance of the calculated mean of viral-cell adherence.

Figure 19:
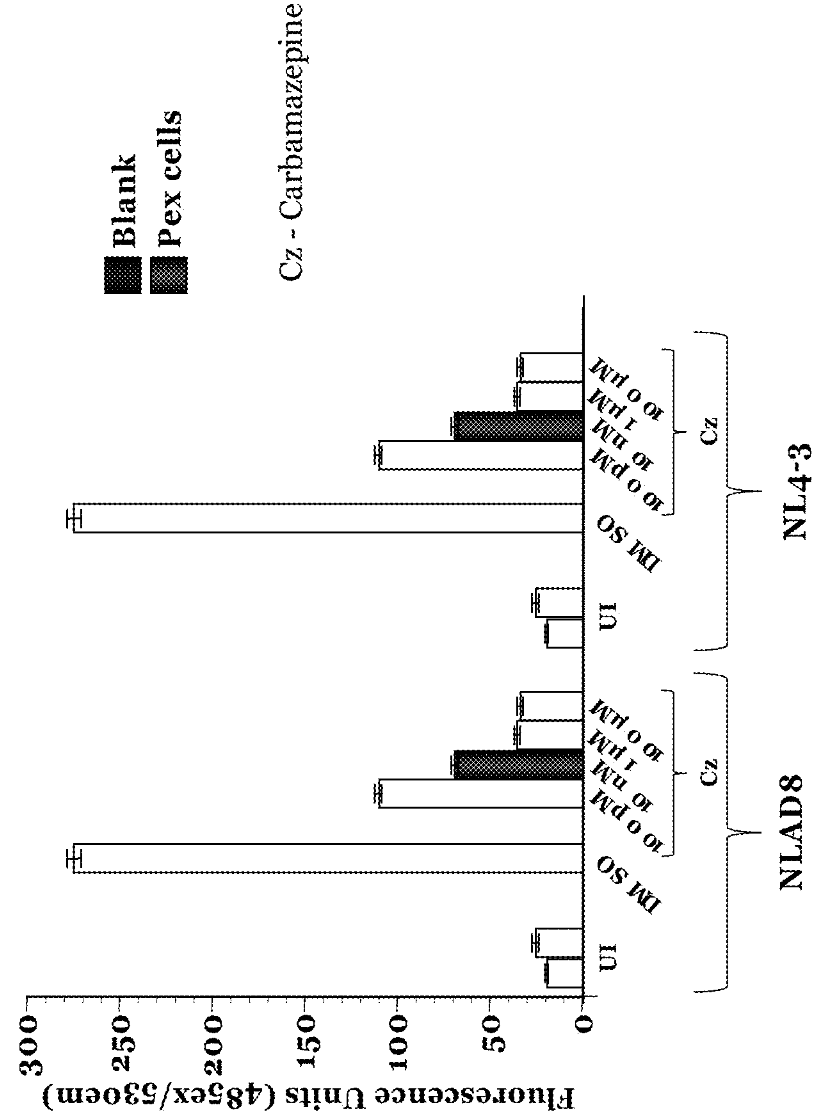
FIG. 19 is a graphical representation showing the effect of carbamazepine on HIV PEX Cell Adherence. A fluorometric adherence assay was used to determine the effect of carbamazepine on HIV adherence to CR3. Arbitrary fluorescence units (y-axis), indicative of adherence, were recorded at 2 h post-challenge of primary human cervical epithelial (i.e., PEX) cells with fluorescently labelled HIV (10 ng of p24 HIV capsid protein equivalent in 100 μL of F12 culture media) strains, NLAD8 and NL4-3. Data shown are the result of 3 separate assays performed in triplicate. A Student's t-test was used to determine the statistical significance of CR3-dependent adherence. A significant ($p \leq 0.0001$) dose-dependent decrease in NLAD8 and NL4-3 HIV adherence to PEX cells was observed in the presence of increasing concentrations carbamazepine.

FIG. 19 shows that a dose-dependent decrease in HIV strains NL4-3 and NLAD8 cell adherence with PEX cells occurred when carbamazepine was included in the assay. The presence of 100 μM carbamazepine decreased NL4-3 cell association to PEX cells by 88.53%±0.37 (P value vs uninfected control=0.01) and for NLAD8 by 87.98%±0.48 (P value vs uninfected control=0.0065). Significant reduction in cell adherence is observed at all concentrations down to 100 μM carbamazepine (for NL4-3 59.65%±0.41 a reduction and for NLAD8 59.65%±0.24). Thus, these data demonstrate that carbamazepine can block NL4-3 and NLAD8 cell adherence to CR3-expressing cells.

Example 11

Figure 20:
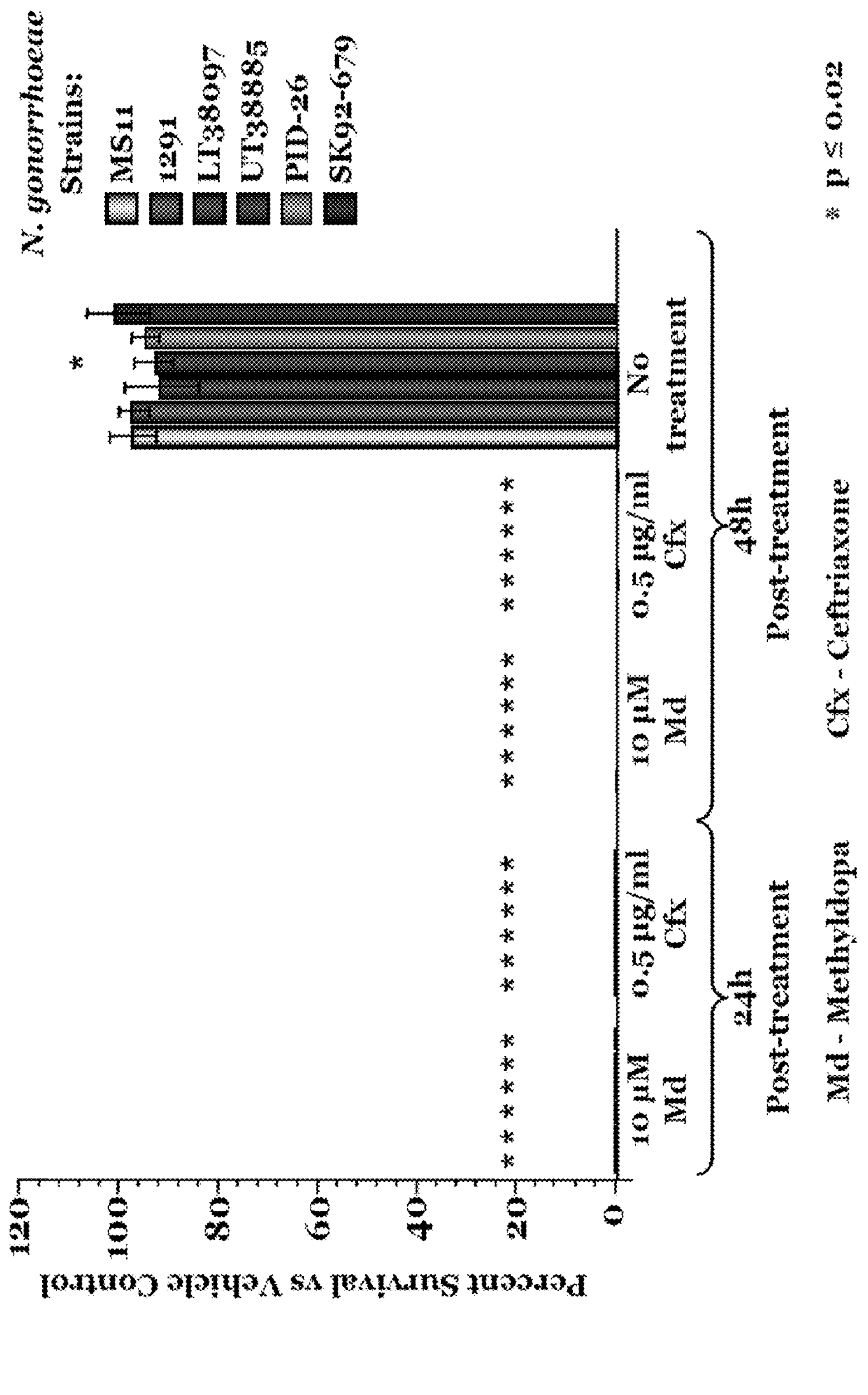
FIG. 20 is a graphical representation showing the effect of single dose methyldopa treatment of PEX cells infected with low-passage *N. gonorrhoeae* isolates. To establish infection, PEX cells were challenged with *N. gonorrhoeae* for 90 min using the noted low-passage isolates. Infections were then allowed to proceed for an additional 24 h or 48 h in the presence or absence of DMSO (1%, vehicle control), methyldopa (10 μM, Md), or ceftriaxone (0.5 μg/mL, positive control, Cfx). The percentage of *N. gonorrhoeae* that survived methyldopa or ceftriaxone treatment (y-axis) was determined as a function of bacteria that survived DMSO treatment at the same time point (set to 100%, not shown). Data shown are the result of 3 separate assays performed in triplicate. A Kruskal-Wallis k-sample analysis of variance was used to determine the statistical significance of bacterial survival. Methyldopa treatment resulted in a significant decrease ($p \leq 0.0001$) in the ability of each strain tested to survive. Greater than 99% gonococcal killing occurred with a 24 h, 10 μM methyldopa treatment.

Single Dose Methyldopa Treatment of PEX Cells Infected with Low-Passage *N. gonorrhoeae* Isolates The ability of a single dose of methyldopa was evaluated to inhibit survival of low-passage *N. gonorrhoeae* isolates in PEX cells challenged with those isolates. To establish infection, PEX cells were challenged with *N. gonorrhoeae* for 90 min using the noted low-passage isolates. Infections were then allowed to proceed for an additional 24 h or 48 h in the presence or absence of DMSO (1%, vehicle control), methyldopa (10 μM, Md), or ceftriaxone (0.5 μg/mL, positive control, Cfx). Inspection of FIG. 20 reveals that treatment of the infected PEX cells with a single dose of methyldopa resulted in a significant decrease ($p \leq 0.0001$) in the ability of each strain tested to survive, with greater than 99% gonococcal killing occurring after a 24 h, 10 μM methyldopa treatment.

Example 12

Single Dose Methyldopa Treatment of PEX Cells Infected with Multidrug-Resistant *N. gonorrhoeae*

Figure 21:
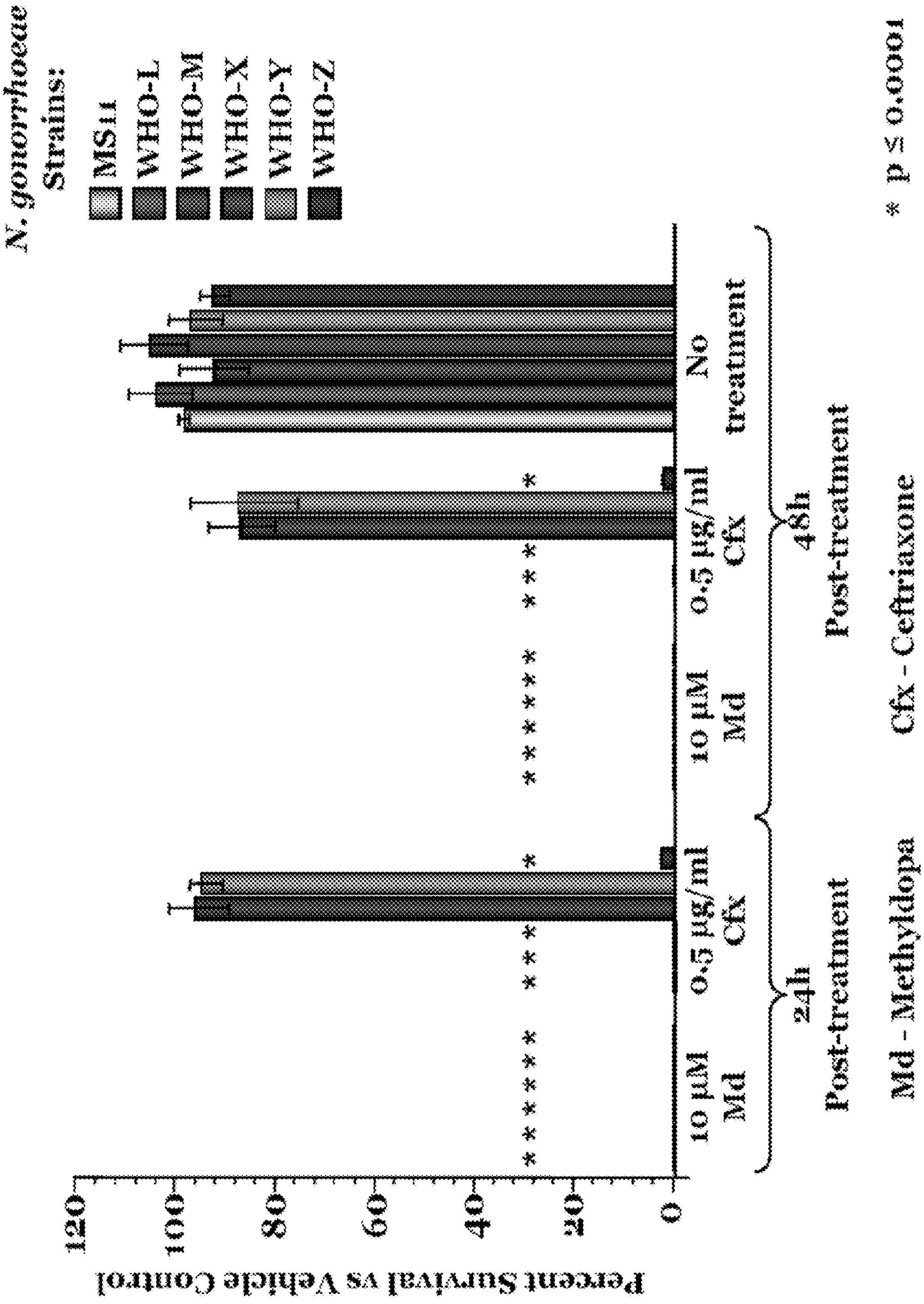
FIG. 21 is a graphical representation showing the effect of single dose methyldopa treatment of PEX cells infected with multidrug-resistant *N. gonorrhoeae*. PEX cells were challenged with the noted multidrug-resistant *N. gonorrhoeae* strains for 90 min to establish infection. Infections were then allowed to proceed for an additional 24 h or 48 h in the presence or absence of DMSO (1%, vehicle control), methyldopa (10 μM, Md), or ceftriaxone (0.5 μg/mL, positive control; Cfx). The percentage of *N. gonorrhoeae* that survived methyldopa or ceftriaxone treatment (y-axis) was determined as a function of bacteria that survived DMSO treatment at the same time point (set to 100%, not shown). Data shown are the result of 3 separate assays performed in triplicate. A Kruskal-Wallis k-sample analysis of variance was used to determine the statistical significance of bacterial survival. Methyldopa treatment resulted in a significant decrease ($p \leq 0.0001$) in the ability of each multidrug-resistant strain tested to survive. Greater than 99% gonococcal killing occurred with a 24 h, 10 μM methyldopa treatment.

The ability of a single dose of methyldopa to inhibit survival of multidrug-resistant *N. gonorrhoeae* strains in infected PEX cells was evaluated using an analogous survival assay to the one described in Example 11. Inspection of FIG. 21 reveals that treatment of the infected PEX cells with a single dose of methyldopa resulted in a significant decrease ($p \leq 0.0001$) in the ability of each multidrug-resistant strain tested to survive, with greater than 99% gonococcal killing occurring after a 24 h, 10 μM methyldopa treatment.

Example 13

Effect of Carbamazepine on *N. gonorrhoeae* in the Absence of Human Cells

Figure 22:
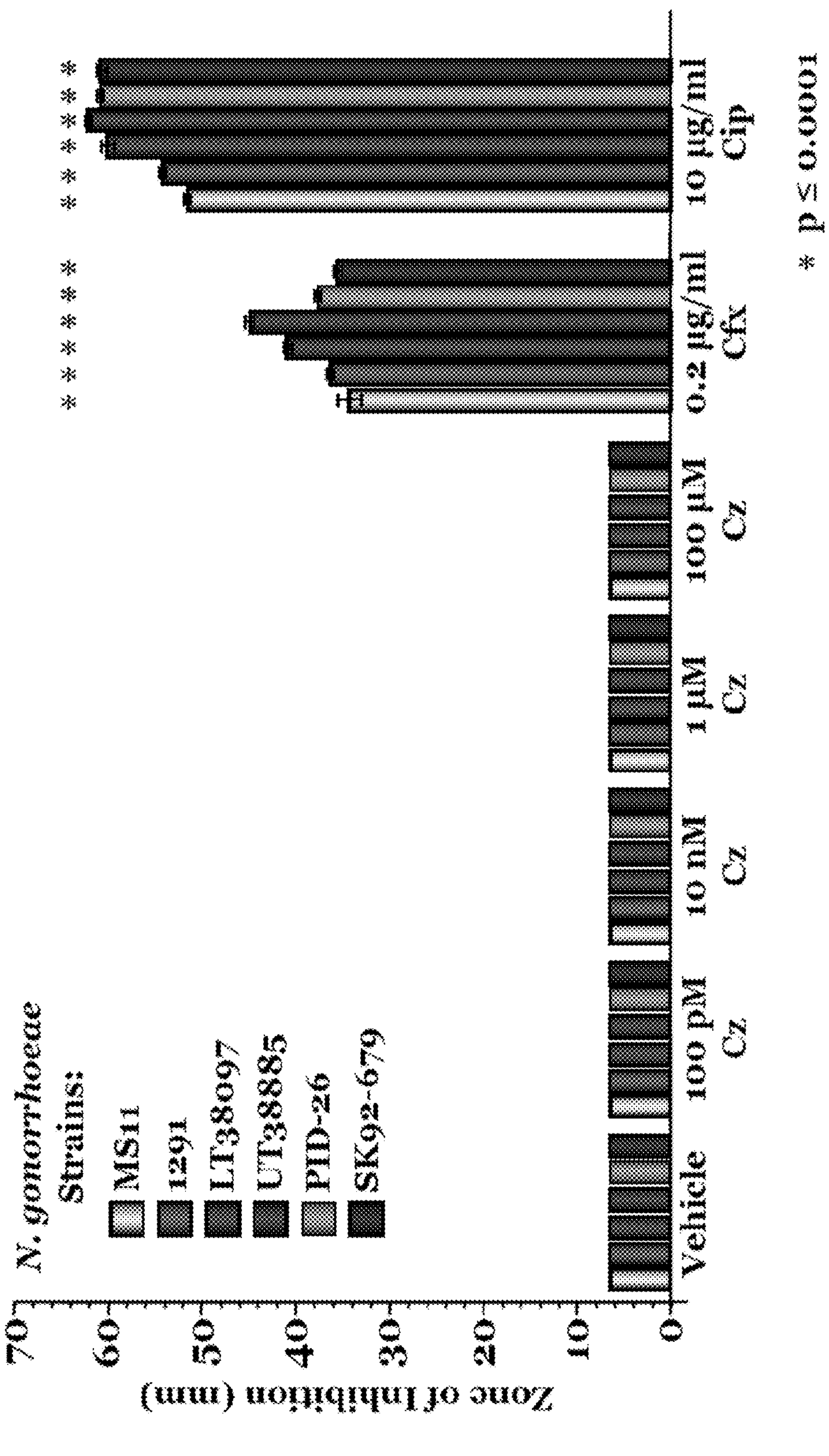
FIG. 22 is a graphical representation showing the effect of carbamazepine on *N. gonorrhoeae* in the absence of human cells. Well diffusion assays were performed in which *N. gonorrhoeae* strains were spread uniformly across the surface of GC-agar plates at a culture density of $10^7$ bacterial per mL. Wells were then punctured within the agar surface to which carbamazepine (Cz; 100 μM to 100 μM, as noted), 0.2 μg/mL ceftriaxone (Cfx), 10 μg/mL ciprofloxacin (Cip), or 1% DMSO (vehicle control) were added. Following an overnight incubation (37° C., 5% CO2), inhibition of *N. gonorrhoeae* growth was measured as the diameter (mm) of the area of clearing surrounding (and inclusive of) each well on each agar plate, i.e., the zone of inhibition (ZOI). For agar plates in which a ZOI was not visible, data were recorded as the diameter of the well (6 mm), as indicated. Assays were performed in triplicate on 3 separate occasions. Data are presented as the mean and variance of the average values obtained for each assay; statistical significance was determined using a Student's t-test. Whereas the traditional antibiotics, ceftriaxone and ciprofloxacin, had a direct effect in killing gonococci, carbamazepine had no effect on the *N. gonorrhoeae* in the absence of human cells. This is consistent with a CR3-dependent, host-mediated mechanism of killing.

Carbamazepine was incubated directly with *N. gonorrhoeae* strains on bacterial growth media to assess whether it had any direct killing or inhibitory effect on the bacteria at concentrations that were used in the blocking and killing assays that were conducted in the presence of human cells. Notably, whereas the traditional antibiotics, ceftriaxone and ciprofloxacin, had a direct effect in killing gonococci, carbamazepine had no effect on the *N. gonorrhoeae* in the absence of human cells (see, FIG. 22). This is consistent with a CR3-dependent, host-mediated mechanism of killing.

Example 14

Effect of Methyldopa on *N. gonorrhoeae* in the Absence of Human Cells

Figure 23:
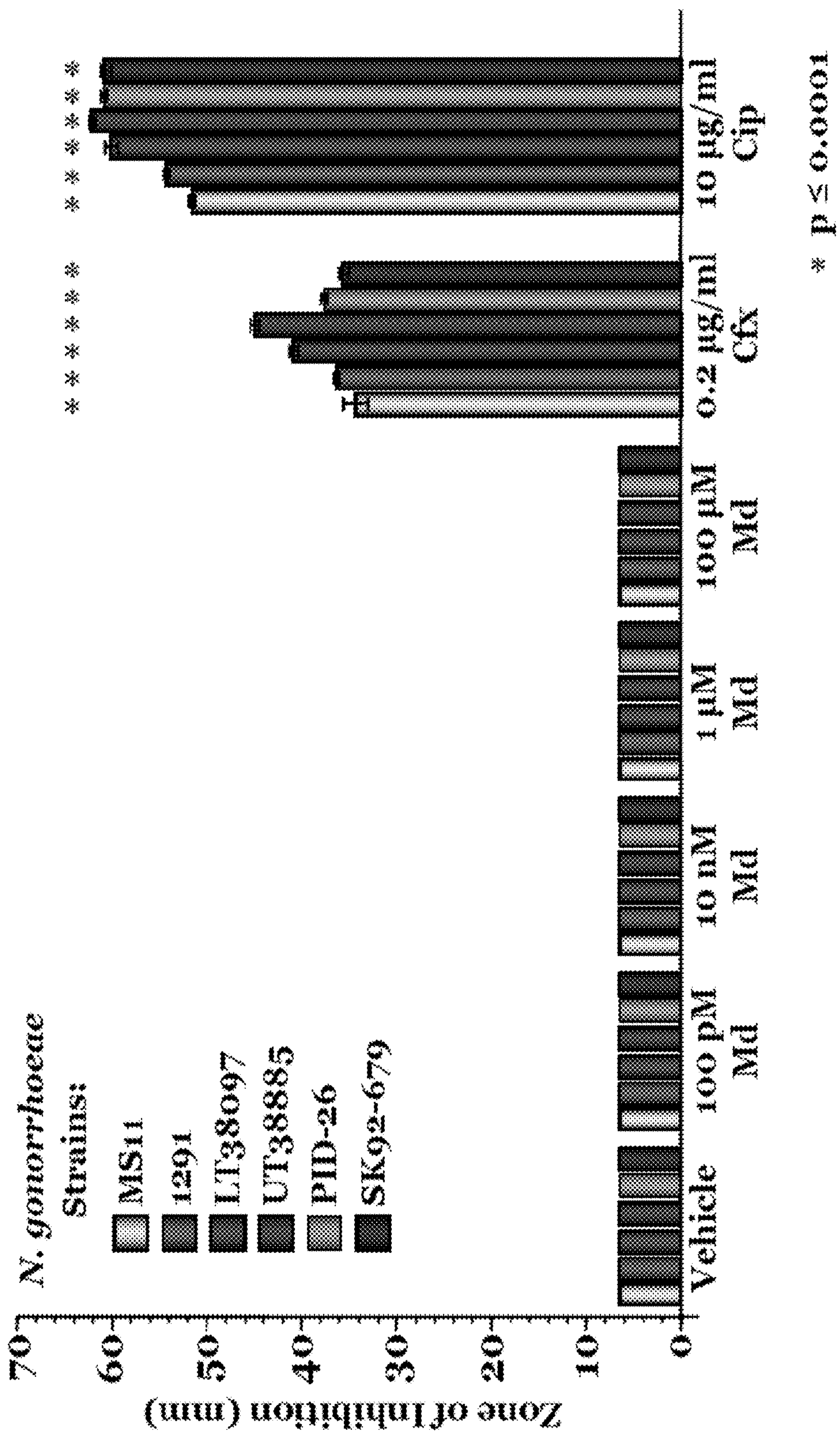
FIG. 23 is a graphical representation showing the effect of methyldopa on *N. gonorrhoeae* in the absence of human cells. Well diffusion assays were performed in which *N. gonorrhoeae* strains were spread uniformly across the surface of GC-agar plates at a culture density of $10^7$ bacterial per mL. Wells were then punctured within the agar surface to which methyldopa (Md; 100 μM to 100 μM, as noted), 0.2 μg/mL ceftriaxone (Cfx), 10 μg/mL ciprofloxacin (Cip), or 1% DMSO (vehicle control) were added. Following an overnight incubation (37° C., 5% CO2), inhibition of *N. gonorrhoeae* growth was measured as the diameter (mm) of the area of clearing surrounding (and inclusive of) each well on each agar plate, i.e., the zone of inhibition (ZOI). For agar plates in which a ZOI was not visible, data were recorded as the diameter of the well (6 mm), as indicated. Assays were performed in triplicate on 3 separate occasions. Data are presented as the mean and variance of the average values obtained for each assay; statistical significance was determined using a Student's t-test. Whereas the traditional antibiotics, ceftriaxone and ciprofloxacin, had a direct effect in killing gonococci, methyldopa had no effect on the *N. gonorrhoeae* in the absence of human cells. This is consistent with a CR3-dependent, host-mediated mechanism of killing.

Methyldopa was incubated directly with *N. gonorrhoeae* strains on bacterial growth media to assess whether it had any direct killing or inhibitory effect on the bacteria at concentrations that were used in the blocking and killing assays that were conducted in the presence of human cells. Consistent with the effects seen with carbamazepine, methyldopa had no effect on the *N. gonorrhoeae* in the absence of human cells, whereas the traditional antibiotics, ceftriaxone and ciprofloxacin, had a direct effect in killing gonococci (see, FIG. 23). This is consistent with a CR3-dependent, host-mediated mechanism of killing.

Example 15

Effect of Flufenamic Acid on *N. gonorrhoeae* in the Absence of Human Cells

Figure 24:
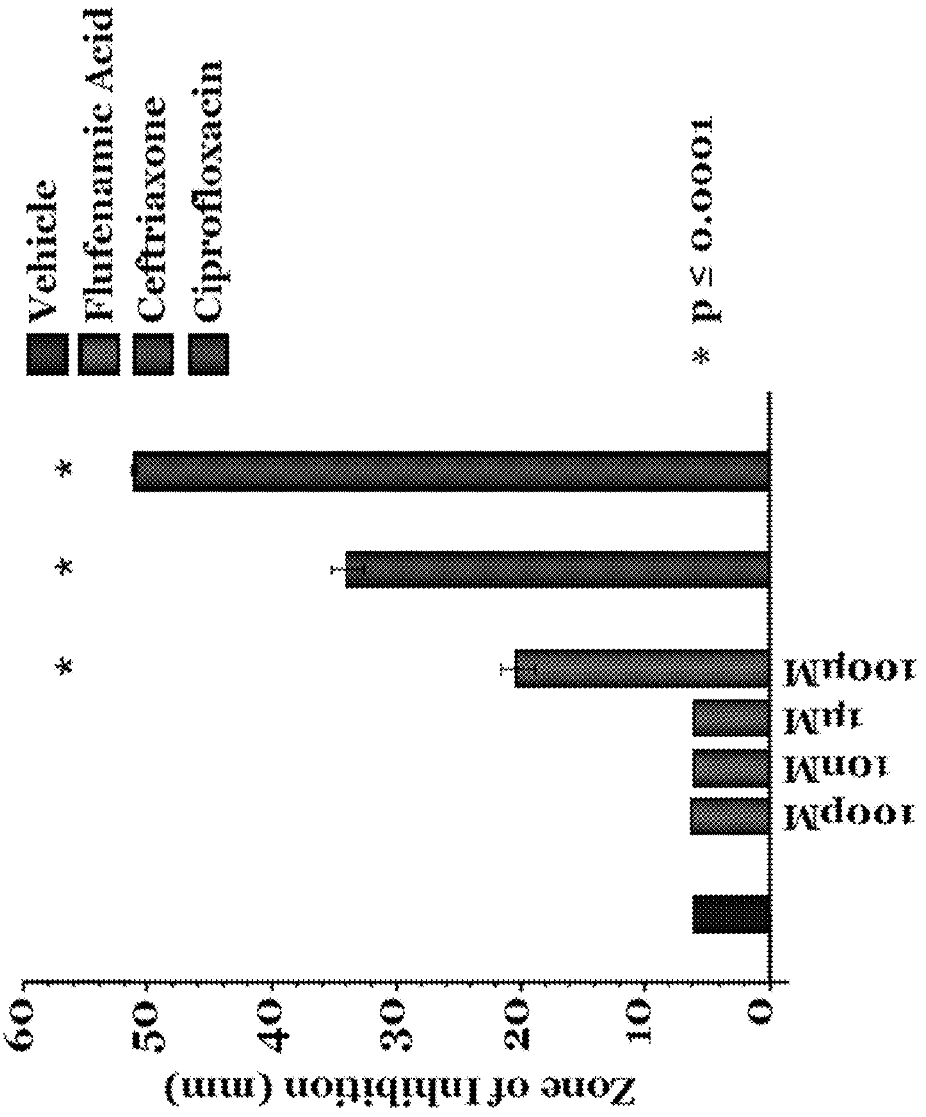
FIG. 24 is a graphical representation showing the effect of flufenamic acid on *N. gonorrhoeae* in the absence of human cells. Well diffusion assays were performed in which *N. gonorrhoeae* strains were spread uniformly across the surface of GC-agar plates at a culture density of $10^7$ bacterial per mL. Wells were then punctured within the agar surface to which flufenamic acid (100 μM to 100 μM, as noted), 0.2 μg/mL ceftriaxone, 10 μg/mL ciprofloxacin, or 1% DMSO (vehicle control) were added. Following an overnight incubation (37° C., 5% CO2), inhibition of *N. gonorrhoeae* growth was measured as the diameter (mm) of the area of clearing surrounding (and inclusive of) each well on each agar plate, i.e., the zone of inhibition (ZOI). For agar plates in which a ZOI was not visible, data were recorded as the diameter of the well (6 mm), as indicated. Assays were performed in triplicate on 3 separate occasions. Data are presented as the mean and variance of the average values obtained for each assay; statistical significance was determined using a Student's t-test. Whereas the traditional antibiotics, ceftriaxone and ciprofloxacin, had a direct effect in killing gonococci, flufenamic acid had no effect on the *N. gonorrhoeae* in the absence of human cells at concentrations of ≤1 μM.

Flufenamic acid was incubated directly with *N. gonorrhoeae* strains on bacterial growth media to assess whether it had any direct killing or inhibitory effect on the bacteria at concentrations that were used in the blocking and killing assays that were conducted in the presence of human cells. Consistent with the effects seen with carbamazepine and methyldopa, flufenamic acid had no effect on the *N. gonorrhoeae* in the absence of human cells, whereas the traditional antibiotics, ceftriaxone and ciprofloxacin, had a direct effect in killing gonococci (see, FIG. 24). This is consistent with a CR3-dependent, host-mediated mechanism of killing.

Materials and Methods

Reagents

Bacteria, HIV and Cell Cultures

PEX cells were procured from surgical cervical tissue and maintained as described previously Edwards et al (2000, *Infect Immun* 68(9):5354-63). De-identified cervical tissues were obtained from the Human Tissue Resource Network (Columbus, OH USA). Chinese hamster ovary (CHO) cells (i.e. CHO-neo, vector control parent cell and CHO-CR3, complement receptor type 3 (CR3)-expressing cells have been described Ingalls et al (1997, *J Immunol.* 159(1):433-

8). CHO cells were maintained in Ham's F12 medium (Gibco, Grand Island, NY USA) supplemented with 5% fetal bovine serum plus 0.5 mg/mL G418 (both from Gibco).

Eleven *N. gonorrhoeae* strains were used in our experiments. These included the laboratory strain, MS11; the low-passage isolates, 1291, UT38097, LT38885, PID-26, and SK92-679; as well as the antibiotic-resistant strains, WHO-L, WHO-M, WHO-X, WHO-Y, and WHO-Z. For use, bacteria were harvested from overnight (37° C., 5% $CO_2$), GC-IsoVitaleX agar plate cultures and enumerated spectrophotometrically, as previously described Edwards et al (2000, *Infect Immun* 68(9):5354-63). Infection studies were performed using a multiplicity of infection of 100 as described in Edwards et al (2000, *Infect Immun* 68(9):5354-63).

Purified HIV derived from mammalian cells (such as HEK-293T, SupT1-CCRS) as previously described Jones et al (2010, *J Biol. Chem.* 285(24):18603-14), Garcia-Minambres et al (2017, *Immunol. Cell Biol.* 95(5):478-48). Two HIV strains have been used for these experiments (NL4-3, and NLADS—Adachi et al (1986, *J Virol.* 59(2):284-91), Freed et al (1995, *J Virol.* 69(6):3949-54). In brief, viruses were purified from ultracentrifugation, and the quantity and infectivity of HIV were measured by HIV p24 protein ELISA and infection in TZM-bl reporter cells as previously described Jones et al (2010, *J Biol. Chem.* 285(24):18603-14), Garcia-Minambres et al (2017, Immunol. Cell Biol. 95(5):478-48). Purified viruses were then used for cell adherence assays. HIV were also fluorescently labelled with either EGFP-Vpr or mCherry-Vpr as previously described Pereira et al (2011, PLoS One 6(2):e17016).

Methods

Fluorometric Adherence Assay

The ability of the compounds, or negative controls to block adherence of *N. gonorrhoeae* strain MS11gfp to PEX cells, CHO-CR3, or CHO-neo cells was evaluated using a fluorometric microtiter plate assay. Assays were performed essentially as described by Jen et al. (2013, *Plos Pathog* 9(5): e1003377). In this regard, GFP-expressing gonococci were used to challenge (1 h) PEX or CHO cells immediately following compound addition. Fluorescence (485/528 nm) intensity, corresponding to bacterial adherence, was recorded using a Synergy HT Multi-mode Microplate Reader (BioTek Instruments, Winooski, VT USA). Blank wells, devoid of PEX or CHO cells, also were inoculated with bacteria and served as a control for non-specific binding. The assay was performed in triplicate on 3 separate occasions. A Student's t-test was used to determine the statistical significance of the calculated mean of bacterial adherence.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method of treating an infection with a pathogen in a subject infected with the pathogen, wherein the pathogen is a *Neisseria* species that interacts with a complement receptor 3 (CR3) polypeptide of a CR3 polypeptide-expressing cell, the method comprising administering to the subject an effective amount of a phenylpropionic acid derivative compound of Formula (III):

(III)

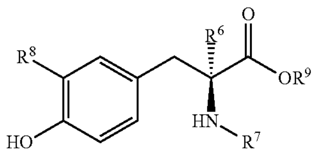

wherein:

$R^6$ is hydrogen, $CH_3$ or $CHF_2$;

$R^7$ is hydrogen or $NH_2$;

$R^8$ is hydrogen or OH;

$R^9$ is hydrogen or $C_{1-4}$alkyl;

or a pharmaceutically acceptable salt or solvate thereof, and wherein the effective amount of the phenylpropionic acid derivative compound is administered to the subject without administering another antimicrobial agent.

2. The method of claim 1, wherein the phenylpropionic acid derivative compound is selected from methyldopa, carbidopa, methyldopa methyl ester, methyldopa ethyl ester, levodopa, etilevodopa (levodopa ethyl ester), metirosine, (α-methyltyrosine) and α-difluoromethyldopa.

3. The method of claim 1, wherein the phenylpropionic acid derivative compound is methyldopa.

4. The method of claim 1, wherein the *Neisseria* species is *Neisseria gonorrhoeae.*

5. The method of claim 1, wherein the *Neisseria* species is multidrug resistant.

6. The method of claim 1, wherein the phenylpropionic acid derivative compound is formulated for oral delivery.

7. The method of claim 1, wherein the phenylpropionic acid derivative compound is formulated for systemic delivery.

8. The method of claim 1, wherein the phenylpropionic acid derivative compound is formulated for topical delivery.

9. The method of claim 1, wherein the phenylpropionic acid derivative compound is formulated for intrauterine delivery.

10. A method of reducing likelihood of developing an infection with a pathogen in a subject not infected with the pathogen but known to be susceptible to the infection and considered likely to develop the infection, or in a subject considered likely to develop a recurrence of a previously treated infection, wherein the pathogen is a *Neisseria* species that interacts with a complement receptor 3 (CR3) polypeptide of a CR3 polypeptide-expressing cell, the method comprising administering to the subject an effective amount of a phenylpropionic acid derivative compound of Formula (III):

(III)

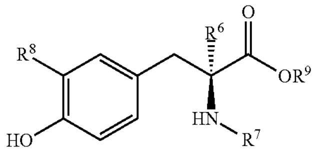

wherein:

$R^6$ is hydrogen, $CH_3$ or $CHF_2$;

$R^7$ is hydrogen or $NH_2$;

$R^8$ is hydrogen or OH;

$R^9$ is hydrogen or $C_{1-4}$alkyl;

or a pharmaceutically acceptable salt or solvate thereof wherein the effective amount of the phenylpropionic acid derivative compound is administered to the subject without administering another antimicrobial agent.

11. The method of claim 10, wherein the phenylpropionic acid derivative compound is selected from methyldopa, carbidopa, methyldopa methyl ester, methyldopa ethyl ester, levodopa, etilevodopa (levodopa ethyl ester), metirosine, (α-methyltyrosine) and α-difluoromethyldopa.

12. The method of claim 10, wherein the phenylpropionic acid derivative compound is methyldopa.

13. The method of claim 10, wherein the *Neisseria* species is *Neisseria gonorrhoeae.*

14. The method of claim 10, wherein the *Neisseria* species is multidrug resistant.

15. The method of claim 10, wherein the phenylpropionic acid derivative compound is formulated for oral delivery.

16. The method of claim 10, wherein the phenylpropionic acid derivative compound is formulated for systemic delivery.

17. The method of claim 10, wherein the phenylpropionic acid derivative compound is formulated for topical delivery.

18. The method of claim 10, wherein the phenylpropionic acid derivative compound is formulated for intrauterine delivery.

* * * * *